(12) United States Patent
Park et al.

(10) Patent No.: US 8,785,392 B2
(45) Date of Patent: Jul. 22, 2014

(54) METHOD FOR INHIBITING CANCER METASTASIS BY ADMINISTRATION OF THE EXTRACELLULAR DOMAIN DLK1 OR A DLK1-FC FUSION PROTEIN

(75) Inventors: Young Woo Park, Daejeon (KR); Kiwon Jo, Yongin-si (KR); Donghee Lee, Suwon-si (KR); Jung Yu, Daejeon (KR); Ji Hyun Park, Yuseong-gu (KR); Chan-Woong Park, Bucheon-si (KR); Eun Jin Kim, Daegu (KR); Yun Jung Park, Gyeonggi-do (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/142,818

(22) PCT Filed: Apr. 13, 2010

(86) PCT No.: PCT/KR2010/002277
§ 371 (c)(1),
(2), (4) Date: Dec. 8, 2011

(87) PCT Pub. No.: WO2011/115323
PCT Pub. Date: Sep. 22, 2011

(65) Prior Publication Data
US 2013/0202592 A1    Aug. 8, 2013

(30) Foreign Application Priority Data

Mar. 16, 2010 (KR) ........................ 10-2010-0023180

(51) Int. Cl.
| A61K 38/16 | (2006.01) |
| A61K 38/17 | (2006.01) |
| A61K 39/00 | (2006.01) |
| C07K 14/435 | (2006.01) |
| C07K 14/705 | (2006.01) |
| C07K 14/735 | (2006.01) |
| C07K 16/28 | (2006.01) |
| C07K 16/00 | (2006.01) |
| C07K 14/475 | (2006.01) |

(52) U.S. Cl.
CPC ............... *C07K 16/00* (2013.01); *C07K 14/435* (2013.01); *C07K 2319/30* (2013.01); *C07K 14/475* (2013.01); *Y10S 530/866* (2013.01); *Y10S 424/809* (2013.01)
USPC ........ 514/19.8; 514/19.2; 514/19.3; 530/350; 530/387.1; 530/866; 424/134.1; 424/178.1; 424/809

(58) Field of Classification Search
None
See application file for complete search history.

(56) References Cited

U.S. PATENT DOCUMENTS

| 5,580,738 A * | 12/1996 | Laborda ........................ 435/6.14 |
| 6,613,565 B1 * | 9/2003 | Witte et al. ................... 435/372 |
| 7,217,798 B2 | 5/2007 | Hinton et al. |
| 7,732,570 B2 | 6/2010 | Hinton et al. |
| 8,017,118 B2 * | 9/2011 | Nakamura et al. ......... 424/133.1 |
| 2002/0064855 A1 | 5/2002 | Lemischka et al. |
| 2009/0299038 A1 | 12/2009 | Nakamura et al. |
| 2009/0326205 A1 | 12/2009 | Nakamura et al. |

FOREIGN PATENT DOCUMENTS

| KR | 10200900888893 | 8/2009 |
| KR | 10-0982170 B1 | 9/2010 |
| WO | 2008056833 A1 | 5/2008 |
| WO | 2009/116670 A1 | 9/2009 |

OTHER PUBLICATIONS

English translation of KR-10-2009-0088893, Aug. 20, 2009; 78 total pages.*
Laborda et al. dlk, a putative mammalian homeotic gene differentially expressed in small cell lung carcinoma and neuroendocrine tumor cell line. J Biol Chem 268(6): 3817-3820, 1993.*
Lee et al. Inhibition of adipogenesis and development of glucose intolerance by soluble preadipocyte factor-1 (Pref-1). J Clin Invest 111: 453-461, 2003.*
Mei et al. Only the large soluble form of preadipocyte factor-1 (Pref-1), but not the small soluble and membrane forms, inhibits adipocyte differentiation: role of alternative splicing. Biochem J 364: 137-144, 2002.*
Smas et al. Cleavage of membrane-associated pref1 generates a soluble inhibitor of adipocyte differentiation. Mol Cell Biol 17(2): 977-988, 1997.*
Yin et al. DLK1: increased expression in gliomas and associated with oncogenic activities. Oncogene 25: 1852-1861, 2006.*
Chen, HC. Boyden chamber assay. Methods Mol Biol 294: 15-22, 2005.*
Shaw, LM. Tumor cell invasion assays. Methods Mol Biol 294: 97-105, 2005.*
International Search Report for PCT/KR2010/002277 mailed May 13, 2011.

(Continued)

*Primary Examiner* — Bridget E Brunner
(74) *Attorney, Agent, or Firm* — Lando & Anastasi LLP

(57) ABSTRACT

A recombinant expression vector, comprising extracellular soluble domain genes of DLK1 and IgG antibody Fc domain genes, is constructed, and DLK1-Fc fusion protein is expressed and purified at 293E cell. The invention confirmed the efficacy as a drug for inhibiting cancer metastasis by confirming markedly reduced migration of cancer cells by DLK1-Fc fusion protein and also computing pharmacokinetic parameters. DLK1-Fc fusion protein has relatively higher stability than non-fusion protein, significantly reduces migration of various cancer cell lines, and provides superior cancer metastasis inhibition effect even at small concentration. Accordingly, DLK1-Fc fusion protein can be used efficaciously as an effective ingredient of a composition for inhibiting cancer metastasis.

5 Claims, 36 Drawing Sheets

(56) References Cited

OTHER PUBLICATIONS

NP_003827 (GI:74136023) "protein delta homolog 1 precursor [Homo sapiens]" GenBank Record created on Feb. 17, 2013 GenBank [online] Bethesda, MD USA: United States National Library of Medicine, retrieved from internet using <http://www.ncbi.nlm.nih.gov/protein/74136023?sat=4&satkey=91016940> GenBank Accession No. NP_003827.3 (GI:74136023).

Wang, et al., "Ectodomain shedding of preadipocyte factor 1 (Pref-1) by tumor necrosis factor alpha converting enzyme (TACE) and inhibition of adipocyte differentiation." Mol Cell Biol. Jul. 2006;26(14):5421-35.

Written Opinion for PCT/KR2010/002277 May 13, 2011.

Dyczynksa, Emilia et al., "Proteolytic Processing of Delta-Like 1 by Adam Proteases" J. Biol Chem., 282 (1): pp. 436-444 (2007).

Li, Liang et al., "Expression of DLK1 in Hematopoietic Cells Results in Inhibition of Differentiation and Proliferation", Oncogene 24, pp. 4472-4476 (2005).

Jensen, C., et al. "Protein Structure of Fetal Antigen 1 (FA1) A novel circulating human epidermal-growth-factor like protein expressed in neuroendocrine tumors and its relation to the gene products of dlk and pG2." Eur. J. Biochem, 225, 83-92 (1994).

* cited by examiner

Fig. 2

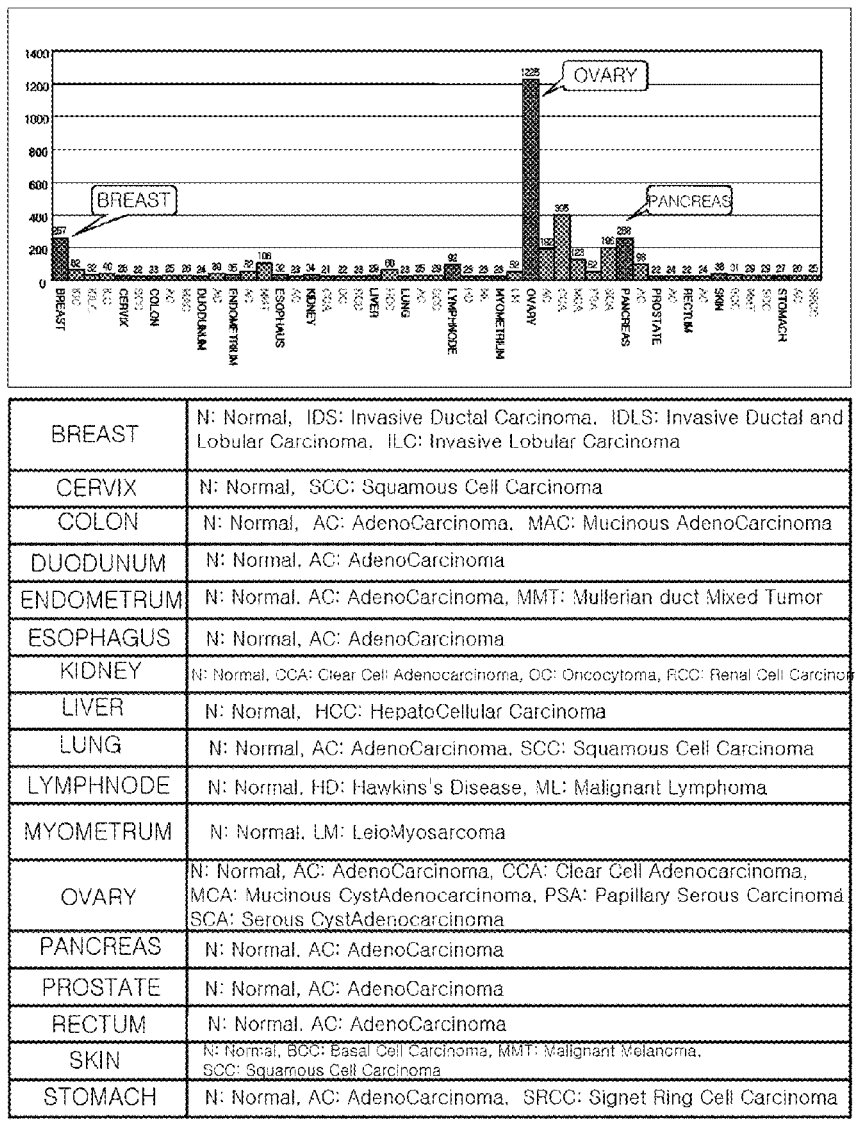

| BREAST | N: Normal, IDS: Invasive Ductal Carcinoma, IDLS: Invasive Ductal and Lobular Carcinoma, ILC: Invasive Lobular Carcinoma |
|---|---|
| CERVIX | N: Normal, SCC: Squamous Cell Carcinoma |
| COLON | N: Normal, AC: AdenoCarcinoma, MAC: Mucinous AdenoCarcinoma |
| DUODUNUM | N: Normal, AC: AdenoCarcinoma |
| ENDOMETRUM | N: Normal, AC: AdenoCarcinoma, MMT: Mullerian duct Mixed Tumor |
| ESOPHAGUS | N: Normal, AC: AdenoCarcinoma |
| KIDNEY | N: Normal, CCA: Clear Cell Adenocarcinoma, OC: Oncocytoma, RCC: Renal Cell Carcinoma |
| LIVER | N: Normal, HCC: HepatoCellular Carcinoma |
| LUNG | N: Normal, AC: AdenoCarcinoma, SCC: Squamous Cell Carcinoma |
| LYMPHNODE | N: Normal, HD: Hawkins's Disease, ML: Malignant Lymphoma |
| MYOMETRUM | N: Normal, LM: LeioMyosarcoma |
| OVARY | N: Normal, AC: AdenoCarcinoma, CCA: Clear Cell Adenocarcinoma, MCA: Mucinous CystAdenocarcinoma, PSA: Papillary Serous Carcinoma, SCA: Serous CystAdenocarcinoma |
| PANCREAS | N: Normal, AC: AdenoCarcinoma |
| PROSTATE | N: Normal, AC: AdenoCarcinoma |
| RECTUM | N: Normal, AC: AdenoCarcinoma |
| SKIN | N: Normal, BCC: Basal Cell Carcinoma, MMT: Malignant Melanoma, SCC: Squamous Cell Carcinoma |
| STOMACH | N: Normal, AC: AdenoCarcinoma, SRCC: Signet Ring Cell Carcinoma |

Fig. 4

| Primer name | Primer Sequence |
|---|---|
| DLK1-F | 5'-CAGGGGGCCGTGGGGGCCGAATGCTTCCCGGCCTGCAA-3' |
| DLK1-R | 5'-TAGCGGCCGACGCGGCCGCCCTCGGTGAGGAGAGGGG-3' |

Fig. 6 gaatgcttcccggcctgcaaccccaaaatggattctgcgaggatgacaatgtttgcaggtgccagcctggctggcagggtc ccctttgtgaccagtgcgtgacctctcccggctgccttcacggactctgtggagaacccgggcagtgcatttgcaccgacgg ctgggacggggagctctgtgatagagatgttcgggcctgctcctcggcccctgtgccaacaacgggacctgcgtgagcct ggacgatggcctctatgaatgctcctgtgccccggggtactcgggaaaggactgccagaaaaaggacggggccctgtgtgat caacggctcccctgccagcacggaggcacctgcgtggatgatgagggccgggcctcccatgcctcctgcctgtgccccc ctggcttctcaggcaatttctgcgagatcgtggccaacagctgcaccccaacccatgcgagaacgacggcgtctgcactg acattgggggcgacttccgctgccggtgcccagccggcttcatcgacaagacctgcagccgcccggtgaccaactgcgcc agcagccgtgccagaacggggggcacctgcctgcagcacacccaggtgagctacgagtgtctgtgcaagcccgagttcac aggtctcacctgtgtcaagaagcgcgcgctgagcccccagcaggtcacccgtctgcccagcggctatgggctggcctacc gcctgacccctggggtgcacgagctgccggtgcagcagccggagcaccgcatcctgaaggtgtccatgaaagagctcaac aagaaaacccctctcctcaccgagggc

Fig. 7

ECFPACNPQNGFCEDDNVCRCQPGWQGPLCDQCVTSPGCLHGLCGEPGQCICTDGWDGE

LCDRDVRACSSAPCANNGTCVSLDDGLYECSCAPGYSGKDCQKKDGPCVINGSPCQHGGT

CVDDEGRASHASCLCPPGFSGNFCEIVANSCTPNPCENDGVCTDIGGDFRCRCPAGFIDKT

CSRPVTNCASSPCQNGGTCLQHTQVSYECLCKPEFTGLTCVKKRALSPQQVTRLPSGYGL

AYRLTPGVHELPVQQPEHRILKVSMKELNKKTPLLTEG

786-O

Migration Condition:
2x10⁴ cells/well, 5% FBS, 24 hrs

UO-31

Migration Condition:
1x10⁵ cells/well, 5% FBS, 24 hrs

A549

Migration Condition:
2x10⁴ cells/well, 5% FBS, 24 hrs

SNU638

Cell    Fc 1 ug    Fc 10 ug

DLK1-Fc 1 ug    DLK1-Fc 10 ug

Migration Condition:
1x10$^5$ cells/well, 10% FBS, 24 hrs

Migration Condition:
5x10⁴ cells/well, 5% FBS, 24 hrs

Fig. 34

| cell line name | cell number | chemoattractant | incubation time(h) |
|---|---|---|---|
| MDA-MB-435 | 20,000 | 10% FBS | 24 |
| Hs578T | 20,000 | 5% FBS | 24 |
| MCF-7 | 100,000 | 5% FBS | 24 |
| HeLa | 50,000 | 10% FBS | 24 |
| SW480 | 100,000 | 5% FBS | 24 |
| 786-O | 20,000 | 5% FBS | 24 |
| HepG2 | 100,000 | 10% FBS | 24 |
| SNU398 | 20,000 | 10% FBS | 24 |
| SNU449 | 100,000 | 5% FBS | 24 |
| MDAH2774 | 50,000 | 5% FBS | 24 |
| IGROV-1 | 100,000 | 5% FBS | 24 |
| Aspc-1 | 100,000 | 10% FBS | 24 |
| HPAC | 100,000 | 5% FBS | 24 |
| MIA paca-2 | 100,000 | 10% FBS | 24 |
| SNU638 | 100,000 | 10% FBS | 24 |
| AGS | 20,000 | 5% FBS | 24 |
| NCIH460 | 100,000 | 5% FBS | 24 |
| NCIH23 | 100,000 | 5% FBS | 24 |
| A549 | 20,000 | 5% FBS | 24 |
| UO-31 | 100,000 | 5% FBS | 24 |
| HT29 | 100,000 | 5% FBS | 24 |

Fig. 36

| | |
|---|---|
| Cmax | 38.96 (ug/ml) |
| Tmax | 4 hr |
| CL(inf)/F | 0.097 |
| t1/2 | 20.675 hr |
| AUC/AUC(inf) | 27.425 hr |

METHOD FOR INHIBITING CANCER METASTASIS BY ADMINISTRATION OF THE EXTRACELLULAR DOMAIN DLK1 OR A DLK1-FC FUSION PROTEIN

CROSS-REFERENCE TO RELATED APPLICATIONS

This is the U.S. National Phase Application under 35 U.S.C. §371 of International Application No. PCT/KR2010/002277, filed Apr. 13, 2010, which claims priority to Korean Patent Application No. KR10-2010-0023180, filed Mar. 16, 2010. The contents of the prior applications are hereby incorporated by reference herein in their entirety.

TECHNICAL FIELD

The present invention relates to a composition for the anti-cancer metastasis containing DLK1-Fc fusion protein which has function to inhibit cancer metastasis.

BACKGROUND ART

Cancer is a major disease that threatens human lives. In South Korea, cancer has been No. 1 cause of death for the past several years. Cancer is the second major cause of death in the U.S.A following the cardiovascular diseases. Although numerous researches have been and are currently conducted, cancer is still the biggest catastrophe that human race has ever suffered, and it takes millions of lives and astronomical costs every year.

Cancer can be referred to as genetic disease in cellular level, considering that the disease develops as genes develop mutations such as oncogenes and tumor suppressor genes. Currently available cancer treatment includes surgery, chemotherapy, radiation therapy and immunotherapy, but the issues related to inhibition of malignant tumor and recurrence thereof have not had efficient solution yet.

One of the most important biological traits of cancer is that the cancer can migrate, and this proposes the biggest obstacle to finding the cure for cancer. In effect, approximately 60% of all the patients with solid tumor showed minute, but clinically-migrated tumor in the diagnosis of primary tumor, and it has been widely recognized that the most critical cause of death of most cancer patients is the metastasis. The process of metastasis involves penetration of tumor to local tissue along with formation of new vessels (i.e., angiogenesis) in which tumor angiogenesis factor (TAF) involves. The vessels newly generated by the tumor have many deficiencies, allowing the cancer cells to easily penetrate. Cancer penetration and metastasis require numerous receptors on cancer cell surfaces such as laminin receptor which is necessary for the adherence to matrix and basement membrane of the tissue, various enzymes necessary to dissolve stroma of normal tissues such as collagenase Type IV, plasminogen activator and cathepsin D, growth factor, autocrine motility factor (AMF), and expression of oncogenes.

Huge expectations are laid on the substances with inhibitory effect on metastasis, but few have actually been developed with an aim to inhibit metastasis. Currently, substances including sulfated polysaccharide, N-diazo acetyl glycin derivative, neuraminidase and fibronectins (FNs) enzyme have been reported of metastasis inhibition effect. But none of these was reported to have been commercialized, and it has not been clarified yet that said substances themselves have such metastasis inhibition effect. If a method for inhibiting migration of cancer efficiently is developed, a treatment that can effectively suppress the deaths by metastasis will be made available.

Meanwhile, delta-like 1 homolog (DLK1), a member of notch/delta/serrate family, is transmembrane glycoprotein encoded in dlk1 located at gene 14q32, and consists of 383 amino acids containing 280 extracellular regions, 24 transmembrane segmemts, and 56 cytoplasmic domains. Among these, there are 6 epidermal growth factor (EGF)-like repeat domains on extracellular region, having 3 N-glycosylation and 7 0-glycosylation sites. As explained, DLK1 is transmembrane protein, but it is also known to be the protein that is an extracellular portion shed from the cellular membrane due to tumor necrosis factor alpha, converting enzyme (TACE) and has a separate function (Yuhui Wang and Hei Sook Sul, Molecular and cellularbiology. 26(14): 5421-5435, 2006).

DLK1 is found in various forms of 50~60 kDa by the glycosylation on the cellular membrane (Smas C M and Sul H S, Cell. 73:725-34, 1993), and has 4 splicing variants by the alternative splicing (Smas C M et al., Biochemistry. 33:9257-65, 1994). Among these, two larger variants have cleavage sites of proteolytic enzymes which are cut by TACE to generate two soluble forms sized to 50 kDa and 25 kDa (Yuhui Wang et al., Journal of Nutrition. 136:2953-2956, 2006) (See FIG. 1).

DLK1 is widely known as fetal antigen 1 (FA1) (Jensen C H et al., European Journal of Biochemistry. 225:83-92, 1994), since this is expressed mainly in developmental stage from embryonic tissue (Smas C M et al., Cell. 73:725-34, 1993; Kaneta M et al., Journal of Immunology. 164:256-64, 2000) and placenta, and particularly in high concentration from maternal serum. Some report expression of DLK1 in glandular cell of pancreas (Kaneta M et al., Journal of Immunology. 164:256-64, 2000), ovary cell, or skeletal myotubes (Floridon C et al., Differentiation. 66:49-59, 2000). DLK1 expression disappears from most tissues after birth, and appears at limited cells such as preadipocyte (Smas C M et al., Cell. 73:725-34, 1993), pancreatic islet cell (Carlsson C at al., Endocrinology. 138:3940-8, 1997) thymic stromal cell (Kaneta M et al., Journal of Immunology. 164:256-64, 2000), or adrenal gland cell (Halder S K et al., Endocrinology. 139: 3316-28, 1998). DLK1 expression is also known as paternal manoallelic expression due to influence by methylation (Schmidt J V at al., Genes and Development. 14:1997-2002, 2000; Takada S et al., Current Biology 10:1135-8, 2000; Wylic A A at al, Genome Research. 10:1711-8, 2000).

DLK1 is widely known as preadipocyte factor-1 (Pref-1) that plays a role of inhibiting differentiation of adipocyte and most frequently researched in that regard (Smas C M et al., Cell. 73:725-34; Villena J A et al., Hormone and Metabolic Research. 34:664-70, 2002). Beside the inhibition of the adipocyte differentiation, DLK1 is also known as it inhibits differentiation of hematopoietic stem cells (Sakajiri S et al., Leukemia. 19:1404-10, 2005; Li L et al., Oncogene. 24:4472-6, 2005), regulates differentiation of lymphoid progenitor cell (Bauer S R et al., Molecular and Cellular Biology. 18:5247-55, 1998; Kaneta M et al., Journal of Immunology. 164:256-64, 2000) and is involved in wound healing (Samulewicz S J et al., Wound Repair and Regeneration. 10:215-21, 2002). However, a little has been studied on the role of DLK1 in relation to cancer cells.

Studies on a link between DLK1 and a few types of cancers has recently reported over-expression of DLK1 in glioma, and the finding that cDNA of DLK1, if over-expressed in glioma, increased proliferation of glioma and thus increased migration (Yin D et al., Oncogene. 25:1852-61, 2006). The report also indicated that DLK1 expression in liver cancer is increased compared to that in normal liver cells, and that by siRNA test, the tumor greatly shrinks when DLK1 expression is decreased (Huang J et al., *Carcinogenesis*. 28(5):1094-1103, 2007). It has been reported recently that the cytoplasmic domain of DLK1 plays an important role in the tumorigenesis (Yuri K et al., *Cancer Research*. 69(24):OF1-10, 2009). Until now, studies about soluble DLK1, which is the extracellular portion shed from the cellular membrane by TACE, have been mainly focused on the function of inhibiting differentiation of adipocyte. The linkage between the extracellular soluble domain of DLK1 and cancer has not been studied yet.

Therefore, the inventors completed the present invention by establishing recombinant expression vector comprising the soluble domain gene in extracellular region of DLK1 with genes of Fc domain of IgG antigen, expressing and purifying DLK1-Fc fusion protein from 293E cell, and confirming markedly decreased migration of cancer cell by DLK1-Fc fusion protein, and efficacy as a drug to inhibit metastasis through measurement of pharmacokinetic (PK) parameters, thereby confirming that the DLK1-Fc fusion protein can be efficaciously used as an effective ingredient of compositions for inhibiting metastasis.

DISCLOSURE

Technical Problem

It is an object of the present invention to provide DLK1-Fc fusion protein and a composition for anti-cancer metastasis containing DLK1-Fc as an effective ingredient.

Technical Solution

To achieve the above-mentioned object, the present invention provides soluble extracellular domain of DLK1 (delta-like 1 homolog).

Further, the invention provides polynucleotide coding extracellular soluble domain of DLK1, a recombinant vector containing the polynucleotide, and a transfected recombinant cell strain in which recombinant vector is transfected into a host cell.

Further, the invention provides extracellular soluble domain of DLK1, and DLK1-Fc fusion protein to which human antibody Fc domain is combined.

Further, the present invention provides polynucleotide which codes the DLK1-Fc fusion protein, a recombinant vector which contains the polynucleotide, and a transfected recombinant cell strain in which the recombinant vector is transfected into a host cell.

Further, the present invention provides a method of preparing DLK1-Fc fusion protein comprising the steps of:
1) culturing a recombinant cell strain; and
2) separating the DLK1-Fc fusion protein from cell strain culture medium.

Further, the present invention provides a composition for anti-cancer metastasis containing the extracellular soluble domain of DLK1 prepared as explained above, or DLK1-Fc fusion protein as an effective ingredient.

Further, the present invention provides a method of inhibiting cancer metastasis comprising a step of administering a pharmaceutically effective amount of extracellular soluble domain of DLK1 or DLK1-Fc fusion protein prepared as explained above into a subject with metastatic tumor.

Further, the present invention provides a use of the extracellular soluble domain of DLK1 or DLK1-Fc fusion protein in preparation of a composition for anti-cancer metastasis.

Advantageous Effects

Compared to non-fusion protein, DLK1-Fc fusion protein of the present invention has high stability, exhibits markedly decreased migration in various cancer cell strains, and has excellent inhibition effect on cancer metastasis even at low concentration, and therefore, can be used as an effective ingredient of a composition for anti-cancer metastasis.

BRIEF DESCRIPTION OF THE DRAWINGS

FIG. 2 shows expression rate of DLK1 gene in tissue of cancer patient.

FIG. 4 shows primer sequence (SEQ. ID. NO. 2: 5' CAGGGGGCCGTGGGGGCCGAATGCTTC-CCGGCCTGCAA-3'; and SEQ. ID. No. 3: 5'-TAGCGGC-CGACGCGGCCGCCCTCGGTGAGGAGAGGGG-3') used in the construction of expression vector for expression of DLK1-Fc fusion protein.

FIG. 6 shows the nucleic acid sequence (SEQ. ID. NO. 1) of the cloned DLK1.

FIG. 7 shows the amino acid sequence (SEQ. ID. NO. 4) of the cloned DLK1.

FIG. 34 shows the number of cells of each cell line, constitution of chemo-attractant, and time of incubation used in the test for confirming cancer migration inhibition effect of the soluble DLK1-Fc fusion protein.

FIG. 36 shows the pharmacokinetic parameters of sDLK1.

BEST MODE

The present invention will be explained in greater detail below.

The present invention provides a soluble domain of extracellular portion of DLK1 (delta-like 1 homolog), a polynucleotide coding the extracellular soluble domain of DLK1, a recombinant vector containing the polynucleotide, and a recombinant cell strain in which the recombinant vector is transfected into a host cell.

The extracellular soluble domain of DLK1 may desirably have amino acid sequence of SEQ. ID. No. 4, but not limited thereto.

The polynucleotide coding the extracellular soluble domain may desirably have gene sequence of SEQ. ID. No. 1, but not limited thereto.

Further, the present invention provides the extracellular soluble domain of DLK1 and a DLK1-Fc fusion protein to which human IgG Fc domain is combined.

The term, "DLK1-Fc fusion protein" refers to a recombinant molecule containing a fragment derived from constant domain of heavy chain of antibody. The Fc fusion protein may include Fc domain of antibody randomly from five Ig class (for Example, IgA, IgD, IgE, IgG and IgM), i.e., include all or part of constant domain of CH2 and CH3. For Example, the DLK1-Fc fusion protein may be prepared into a form containing all or part of constant domain of heavy chain in carboxy- and amino-terminal of extracellular soluble domain of DLK1. As for another Example, the Fc fusion protein may include a form containing constant domain portion of two or more of heavy chain of antibody, and herein, two heavy chains of Fc may be connected by disulfide bond or covalent bond. As for another example, DLK1 part of the DLK1-Fc fusion protein may include a form containing two or more extracellular soluble domains of DLK1.

Further, the present invention provides a polynucleotide coding the DLK1-Fc fusion protein, a recombinant cell strain containing the polynucleotide, and a transfected recombinant vector in which recombinant vector is transfected into a host cell.

Further, the present invention provides a method for preparing DLK1-Fc fusion protein comprising steps of:
1) culturing a recombinant cell strain; and
2) separating DLK1-Fc fusion protein from cell strain culture media.

The expression vector containing the gene may desirably be pYK602-His vector, but not limited thereto. Any vector may be used, provided that the vector includes expression promoter, Fc domain of mammal.

The cell of mammal may desirably be 293E cell, but not limited thereto. Any mammal cell strain, in which a promoter is operative, may be used.

Figure 1:
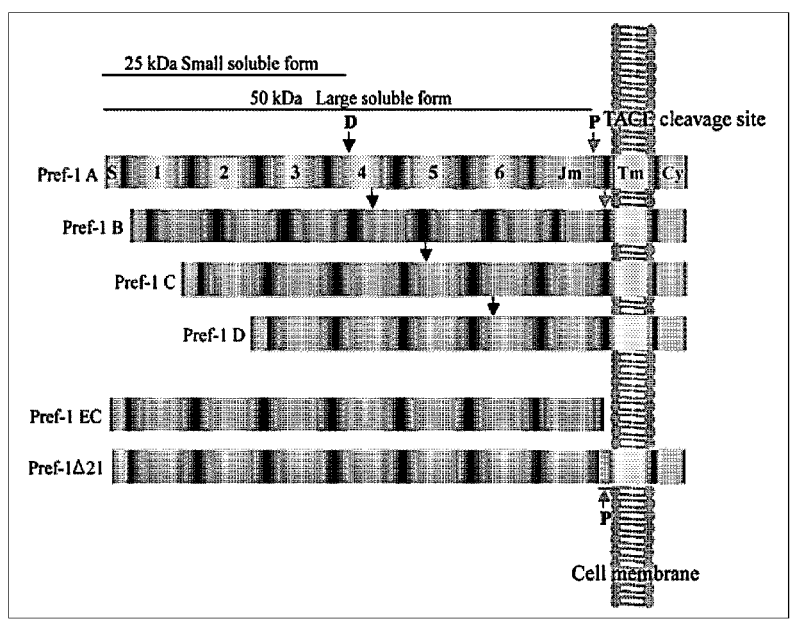
FIG. 1 illustrates the structure of DLK1 protein, where:
S: signal peptide
1-6: epidermal growth factor (EGF)-like repeat domains
JM: juxtamembrane domain
Tm: transmembrane domain
Cy: intracellular domain
Figure 3:
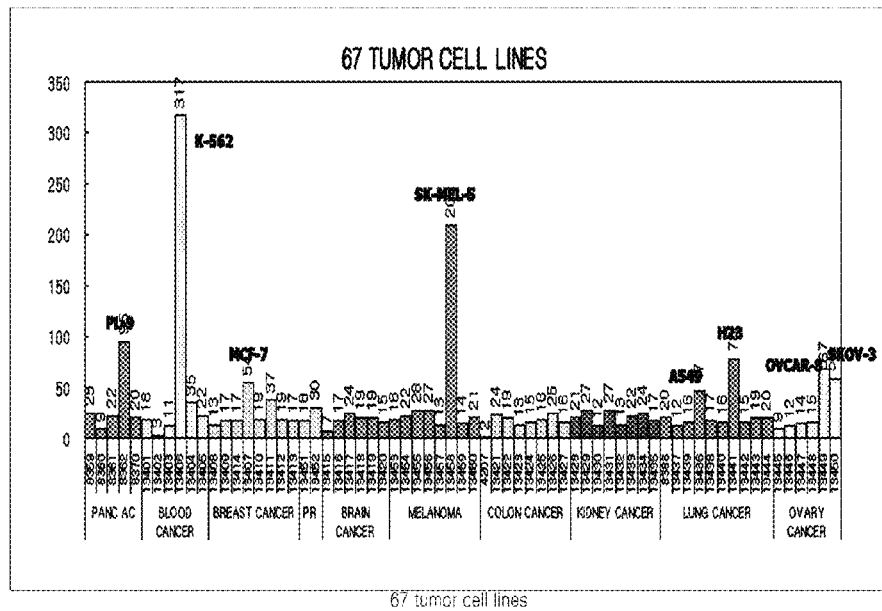
FIG. 3 shows expression rate of DLK1 gene in cancer cell.

Based on the microarray result in the precedent study of the inventors, in contrast to the prior documentations, the expression of DLK1 (see FIG. 2) was rather decreased, and such phenomenon was particularly observed in tissues of breast cancer, pancreatic cancer and ovarian cancer (FIG. 2). Also, except for a few cell strains, the expression was very low in 67 cancer cell strains (see FIG. 3). In view of the above pattern of expression, the possibility of DLK1 to function as tumor suppressor gene as well as an oncogene can be expected. The study particularly used only the soluble domain which were the outer part of cell membrane shed from the cell membrane by tumor necrosis factor alpha converting enzyme (TACE) and thus had paracrine effect as well as autocrine effect.

Soluble Fc fusion protein is widely used in in vitro experiment and in vivo experiment, and has many merits for having higher stability, especially in animal experiments, compared to non-fusion protein (Meg L et al., Methods in Molecular Biology 378:33-52, 2007). The soluble Fc fusion protein is currently widely used, since this retains antigenic specificity in generation of human antibody medicine while excluding many immunological problems. Representative soluble Fc fusion human antibody medicine is Etanercept, a medicine for arthritis of Amgen, which is made by amalgamating a soluble domain of TNF receptor 2 with Fc of human IgG1 (U.S. Pat. No. 5,447,851).

Figure 5:
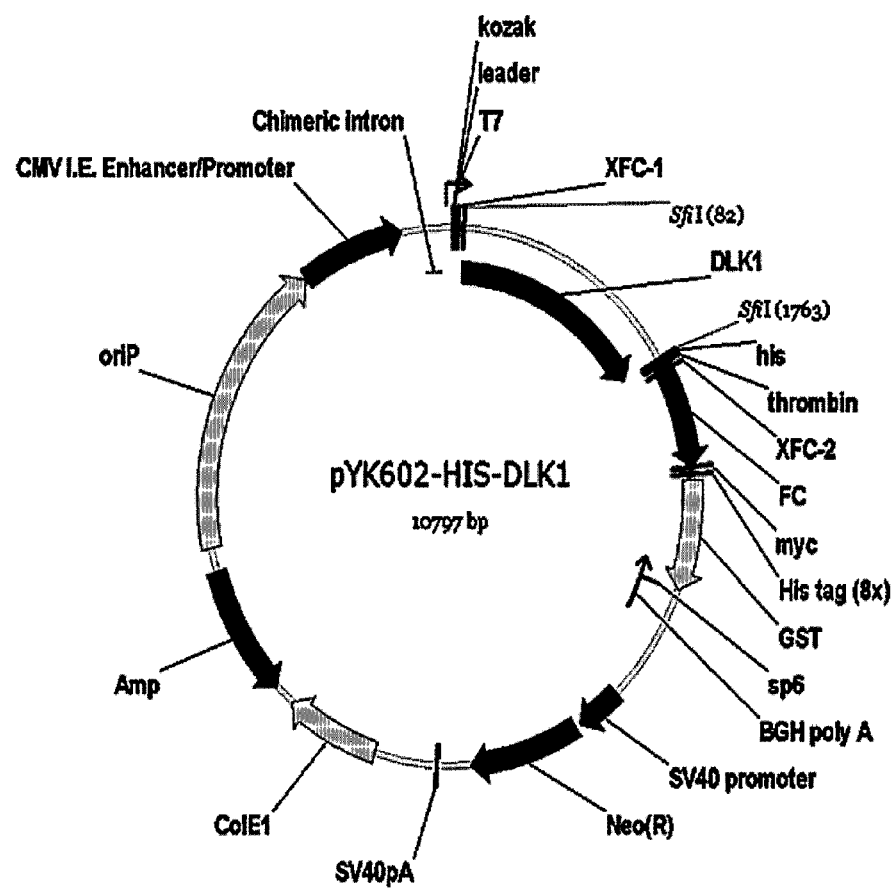
FIG. 5 shows the structure of pYK602-His-DLK1 vector, which is the expression vector for the expression of DLK1-Fc fusion protein.

In a particular example of the present invention, in order to clone DLK1 into pYK602-His vector, polymerase chain reaction (PCR) was conducted using DNA library mix (of kidney, placenta, pancreas and liver) as a template, using primer of SEQ. ID. NO. 2(5'-CAGGGGGCCGTGGGGGCCGAAT-GCTTCCCGGCCTGCAA-3') and SEQ. ID. No. 3(5'-TAGCGGCCGACGCGGCCGCCCTCGGT-GAGGAGAGGGG-3') to selectively amplify the extracellular soluble domain of DLK1 protein, and restriction enzyme reaction was carried out on the product of the PCR using SfiI, and pYK602-His-DLK1 recombinant vector was established by combining pYK602-His-DLK1 (FIGS. 4 and 5).

Figure 8:
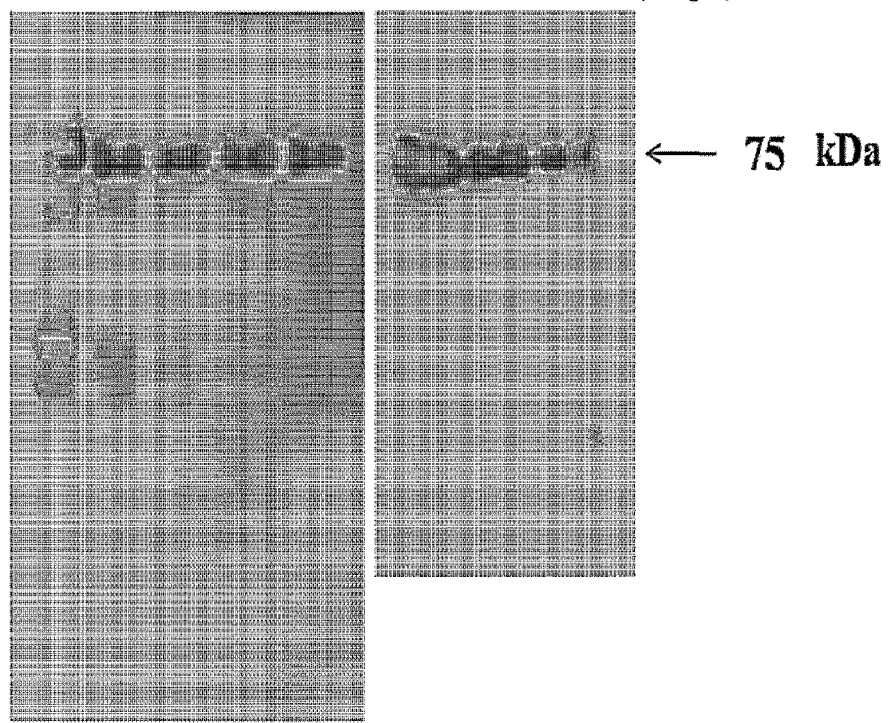
FIG. 8 shows the expression of DLK1-Fc fusion protein obtained from the cell culture medium which is recovered after induction of DLK1-Fc fusion protein expression of 293E cell.
Figure 9:
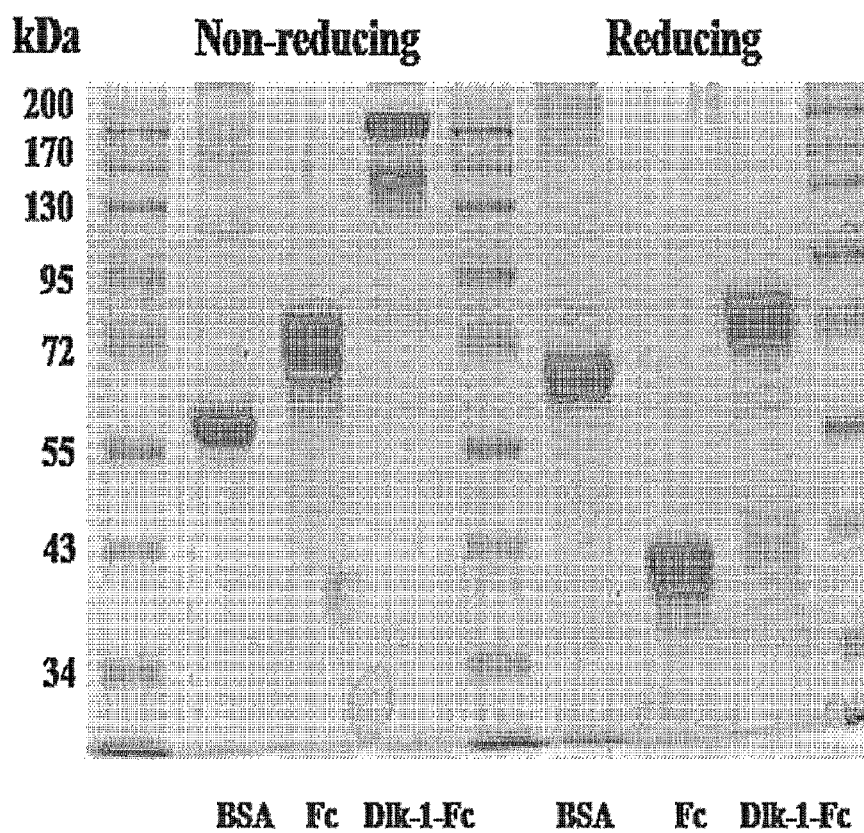
FIG. 9 shows the result of SDS-polyacrylamide gel to confirm the purified DLK1-Fc fusion protein.

After that, pYK602-His-DLK1 DNA was transfected into 293E cell, media was recovered, and expression of DLK1-Fc fusion protein was observed by Western Blotting (FIG. 8). Purification was carried out using protein A column with respect to the media with confirmed expression, pH of the purified DLK1-Fc protein was neutralized, dialysis was carried out using potassium phosphate saline (PBS) buffer, quantification was carried out through BCA analysis and completion of purification and quantification was confirmed by SDS-PAGE (FIG. 9). After that, bacterial endotoxin was removed using EndoTrap Red column from the purified DLK1-Fc fusion protein. As a result, DLK1-Fc fusion protein was prepared.

Further, the present invention provides a composition for inhibiting cancer metastasis comprising an extracellular soluble domain of the DLK1 prepared as explained above, or the DLK1-Fc fusion protein as an effective ingredient.

The cancer may be at least one selected from a group consisting of skin cancer, liver cancer, stomach cancer, breast cancer, colon cancer, cancer of a bone, pancreatic cancer, head cancer or neck cancer, uterine cancer, colon cancer, lung cancer, ovarian cancer, cancer of rectum, cancer of esophagus, cancer of small bowel, anal cancer, colon cancer, cancer of fallopian tube, endometrial carcinoma, cervical carcinoma, vaginal cancer, vulva cancer, Hodgkin's disease, prostate cancer, bladder cancer, kidney cancer, ureteral cancer, renal cell carcinoma, renal pelvic carcinoma, and tumors of central nervous system, and more preferably, one selected from a group consisting of skin cancer, breast cancer, uterine cancer, colon cancer, kidney cancer, liver cancer, lung cancer, ovarian cancer, stomach cancer, and pancreatic cancer, but not limited thereto.

Figure 14:
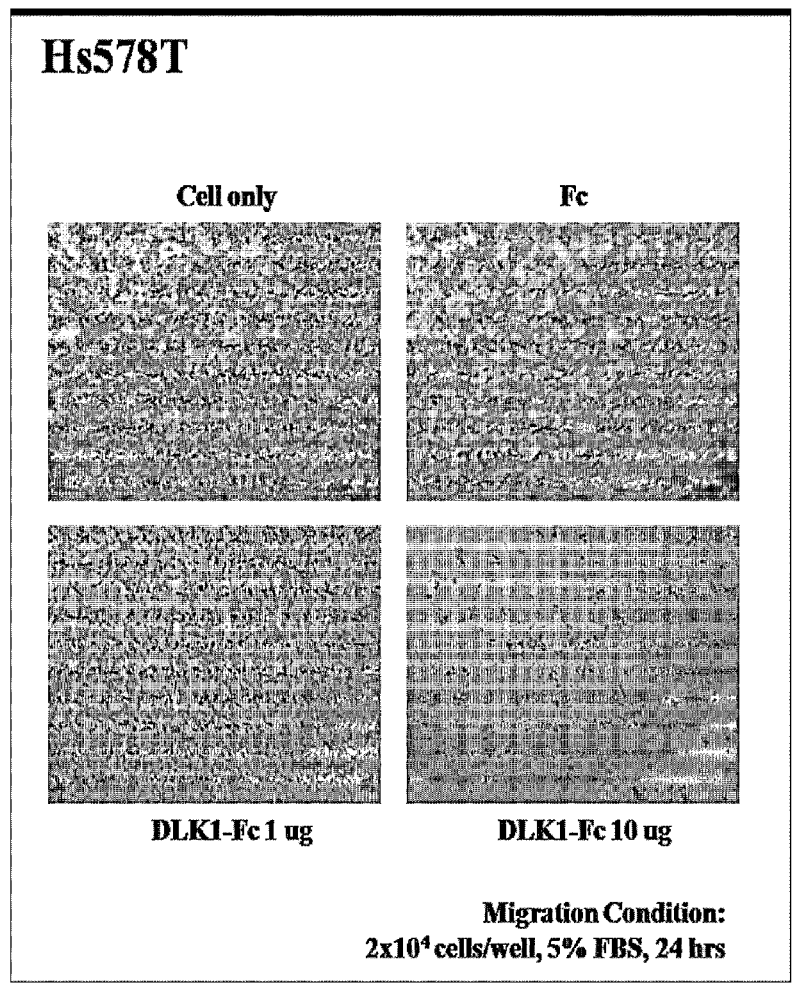
FIG. 14 shows the migration inhibition effect of the cell culture medium containing soluble DLK1-Fc fusion protein in breast cancer cell line (Hs578T).
Figure 15:
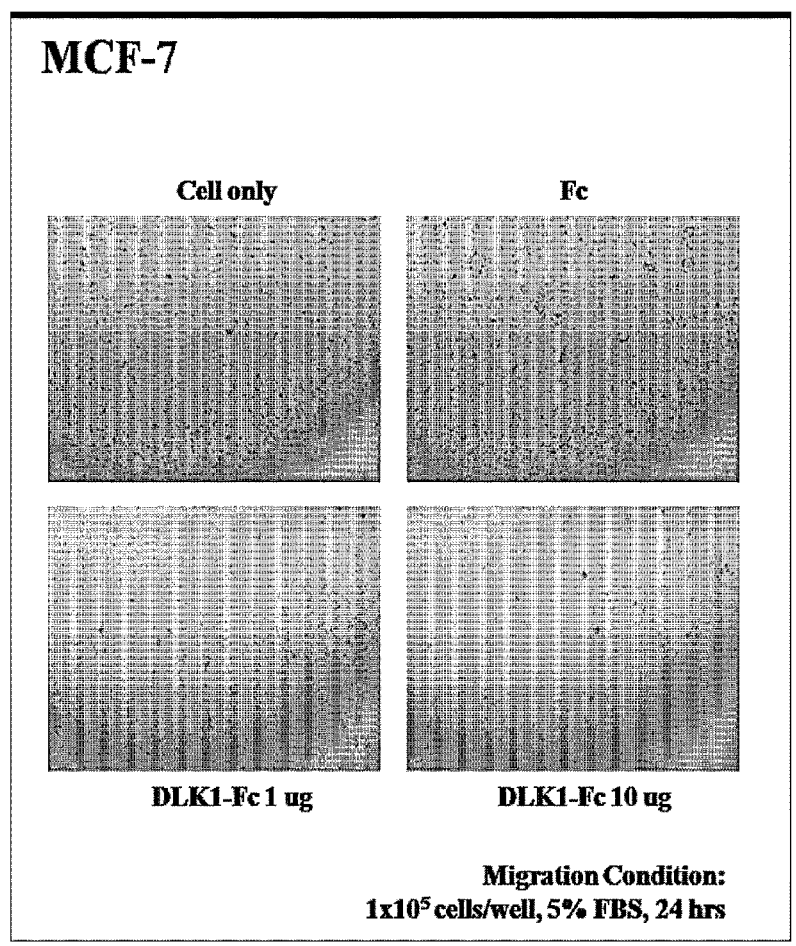
FIG. 15 shows the migration inhibition effect of the cell culture medium containing soluble DLK1-Fc fusion protein in breast cancer cell line (MCF-7).
Figure 16:
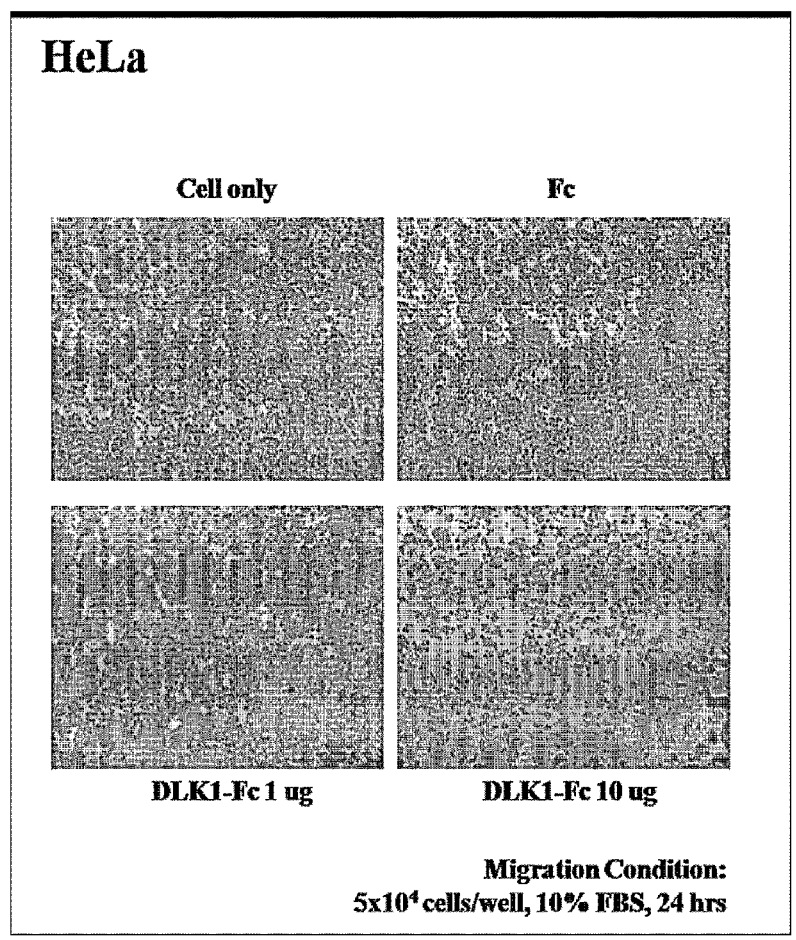
FIG. 16 shows the migration inhibition effect of the cell culture medium containing soluble DLK1-Fc fusion protein in uterine cancer cell line (HeLa).
Figure 17:
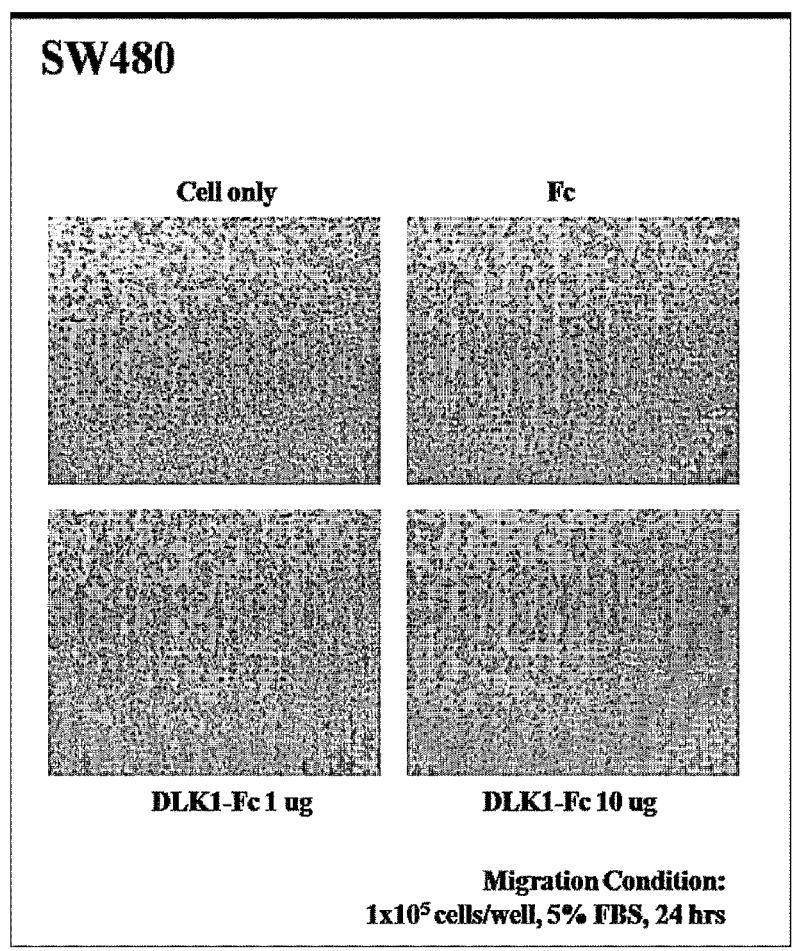
FIG. 17 shows the migration inhibition effect of the cell culture medium containing soluble DLK1-Fc fusion protein in colon cancer cell line (SW480).
Figure 18:
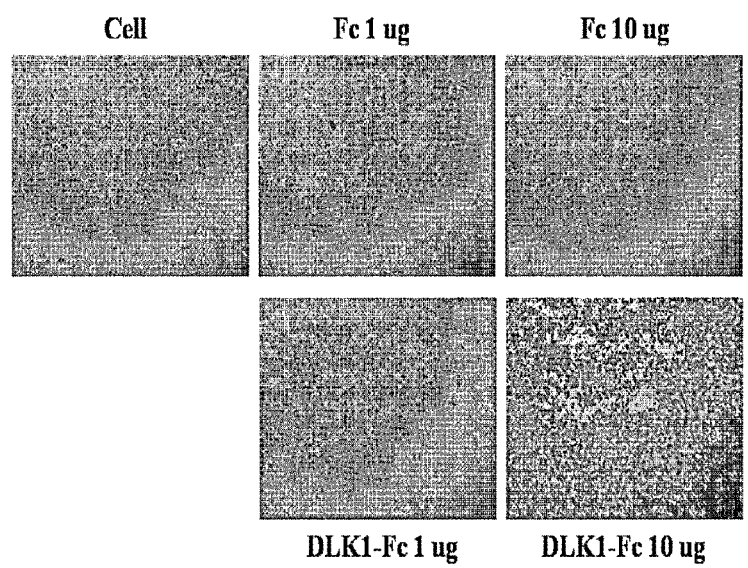
FIG. 18 shows the migration inhibition effect of the cell culture medium containing soluble DLK1-Fc fusion protein in colon cancer cell line (HT29).
Figure 19:
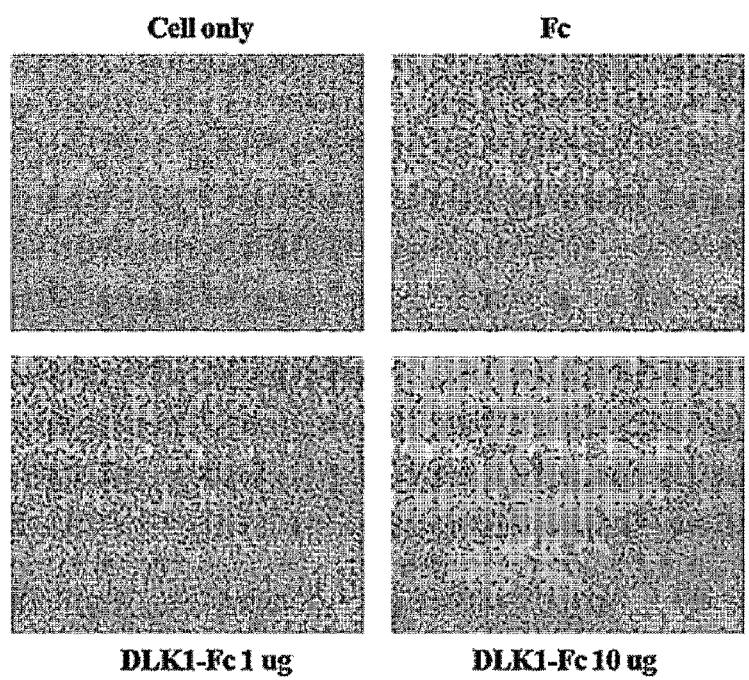
FIG. 19 shows the migration inhibition effect of the cell culture medium containing soluble DLK1-Fc fusion protein in kidney cancer cell line (786-O).
Figure 20:
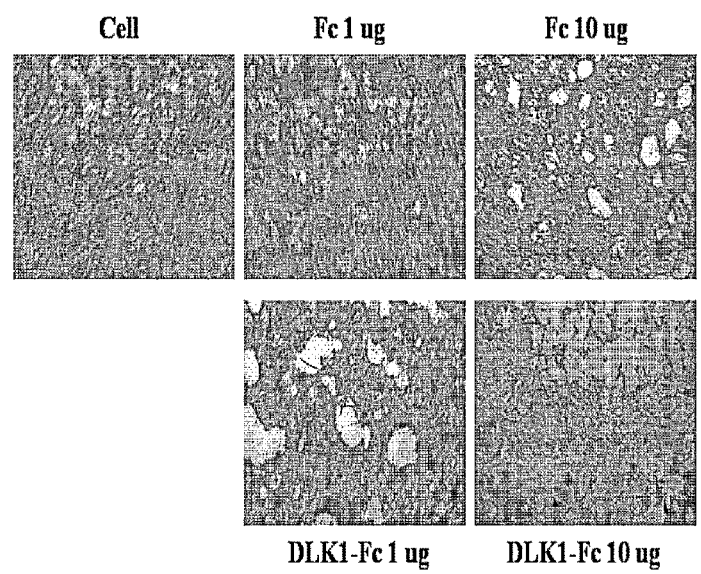
FIG. 20 shows the migration inhibition effect of the cell culture medium containing soluble DLK1-Fc fusion protein in kidney cancer cell line (UO-31).
Figure 22:
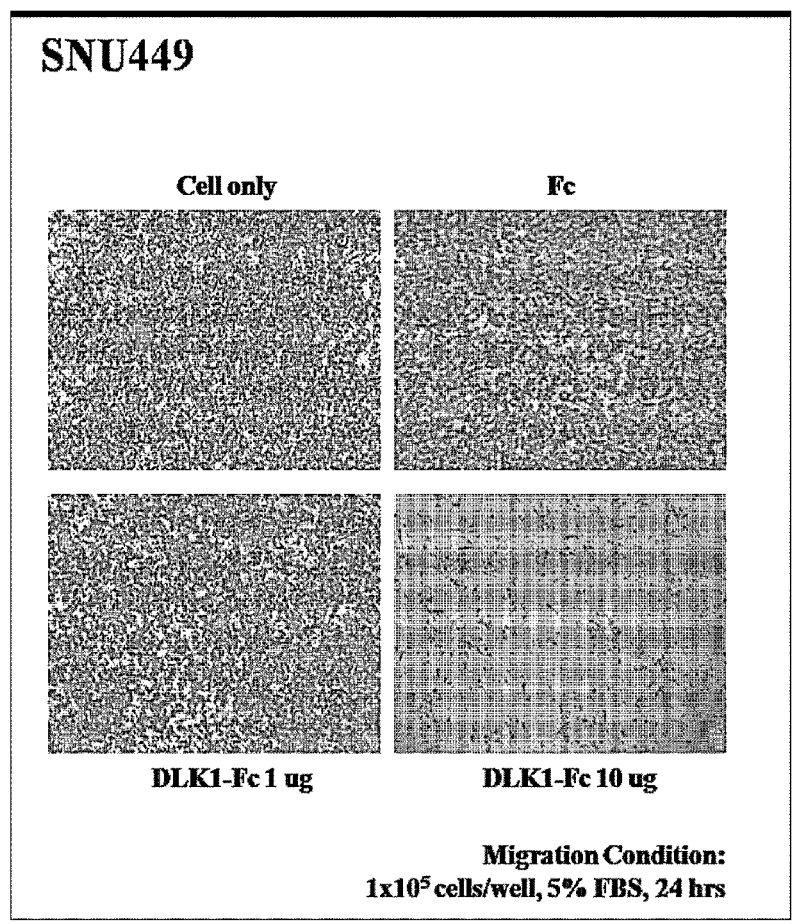
FIG. 22 shows the migration inhibition effect of the cell culture medium containing soluble DLK1-Fc fusion protein in liver cancer cell line (SNU449).
Figure 23:
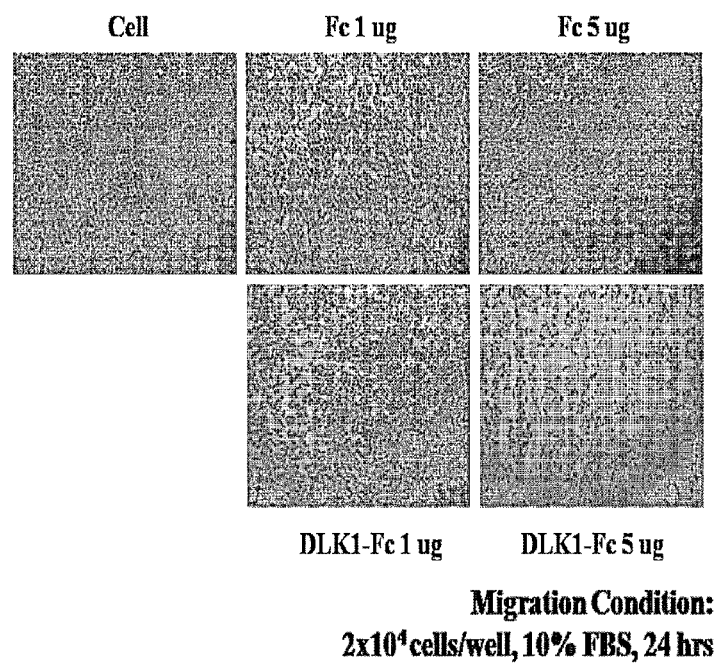
FIG. 23 shows the migration inhibition effect of the cell culture medium containing soluble DLK1-Fc fusion protein in liver cancer cell line (SNU398).
Figure 24:
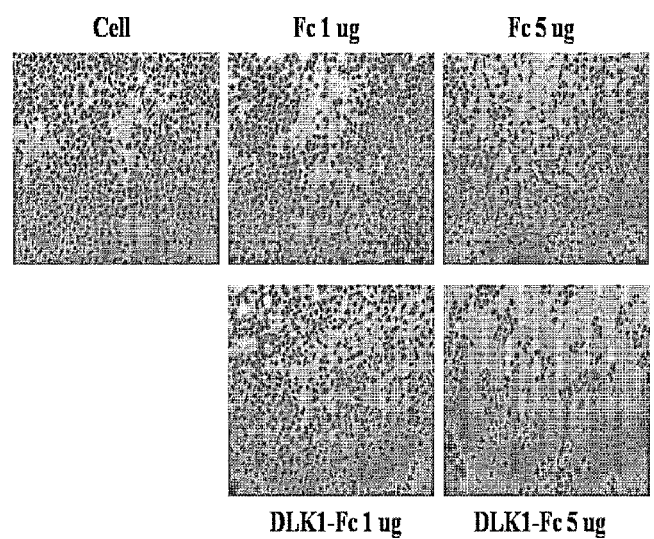
FIG. 24 shows the migration inhibition effect of the cell culture medium containing soluble DLK1-Fc fusion protein in lung cancer cell line (A549).
Figure 25:
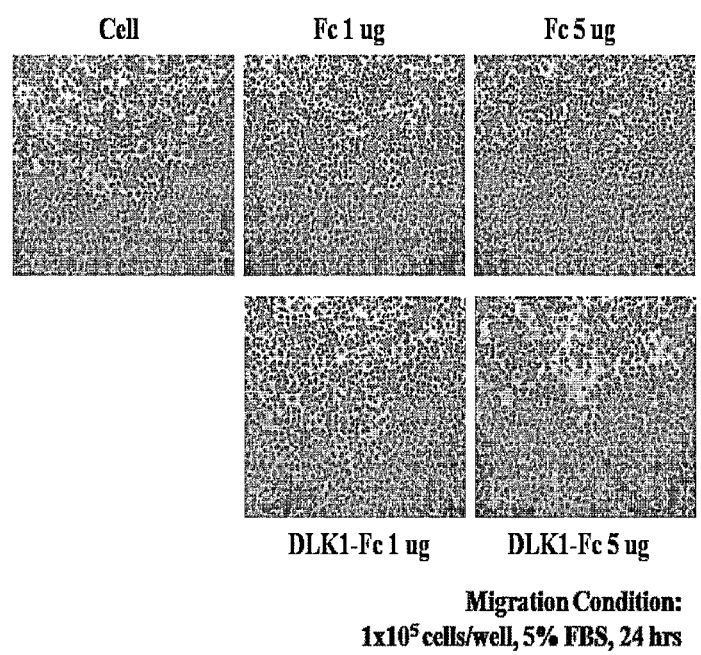
FIG. 25 shows the migration inhibition effect of the cell culture medium containing soluble DLK1-Fc fusion protein in lung cancer cell line (NCIH23).
Figure 26:
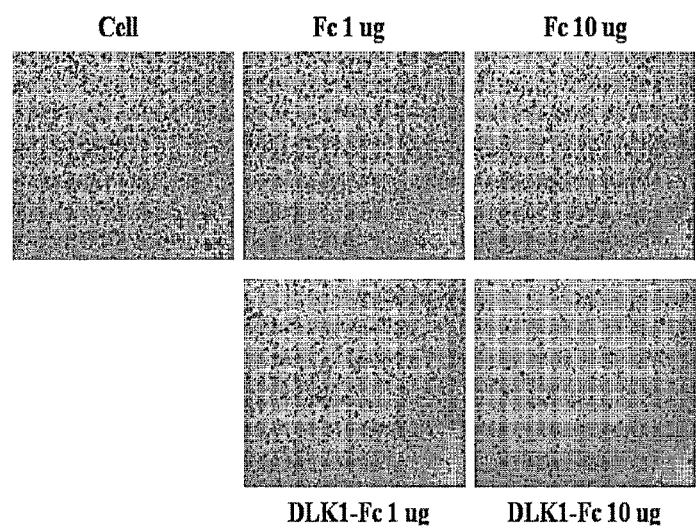
FIG. 26 shows the migration inhibition effect of the cell culture medium containing soluble DLK1-Fc fusion protein in lung cancer cell line (NCIH460).
Figure 27:
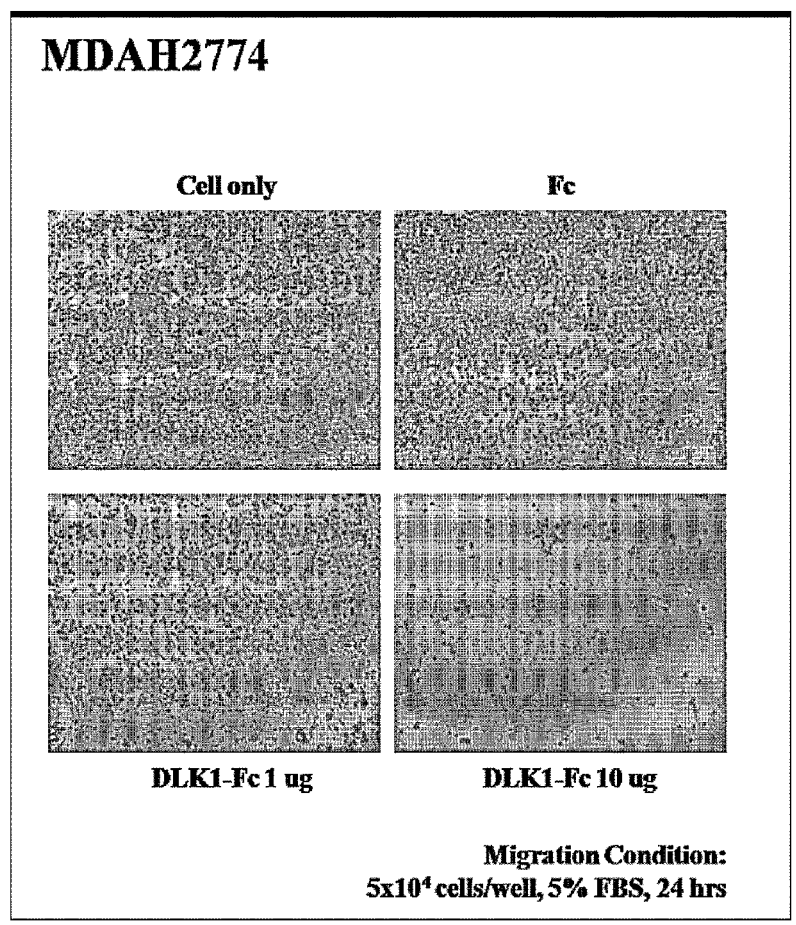
FIG. 27 shows the migration inhibition effect of the cell culture medium containing soluble DLK1-Fc fusion protein in ovarian cancer cell line (MDAH2774).
Figure 28:
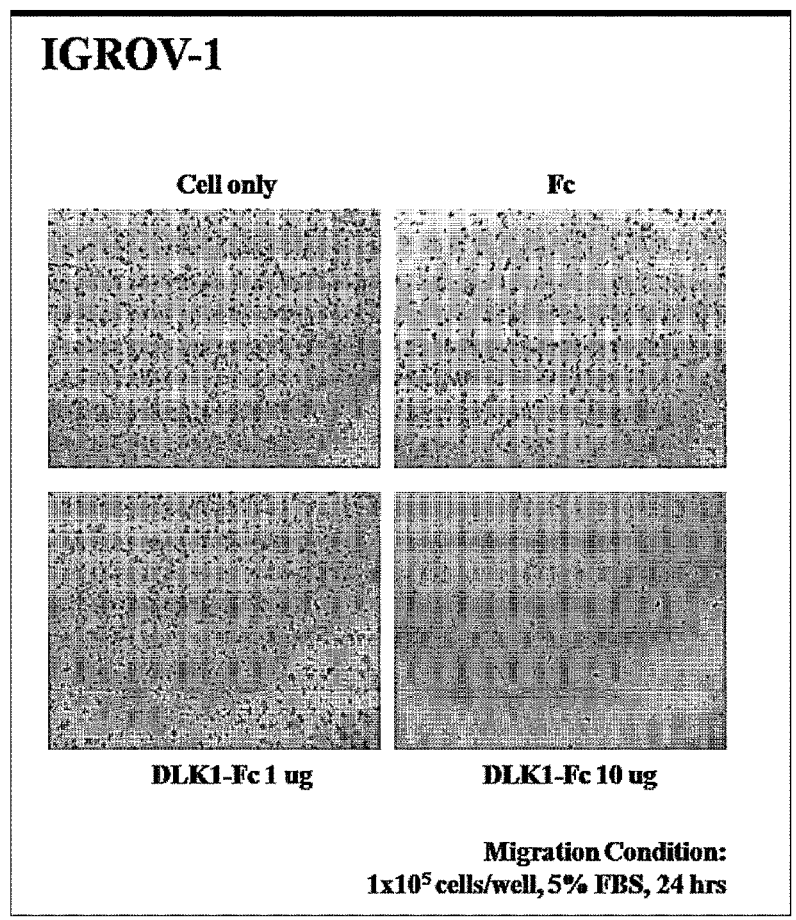
FIG. 28 shows the migration inhibition effect of the cell culture medium containing soluble DLK1-Fc fusion protein in ovarian cancer cell line (IGROV-1).
Figure 29:
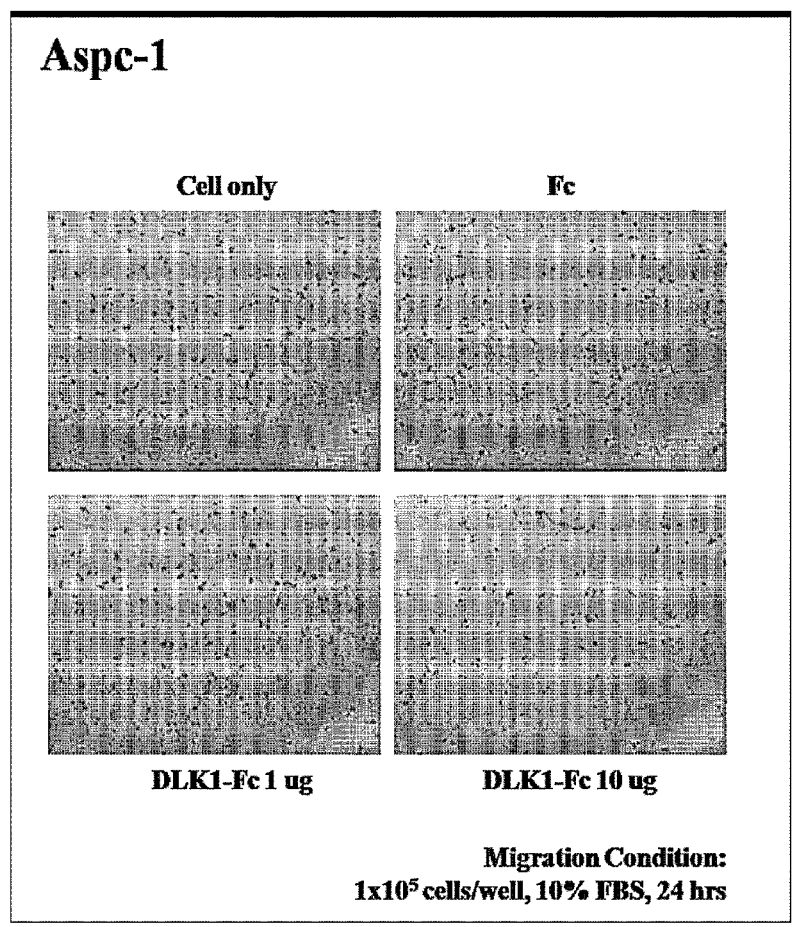
FIG. 29 shows the migration inhibition effect of the cell culture medium containing soluble DLK1-Fc fusion protein in pancreatic cancer cell line (Aspc-1).
Figure 30:
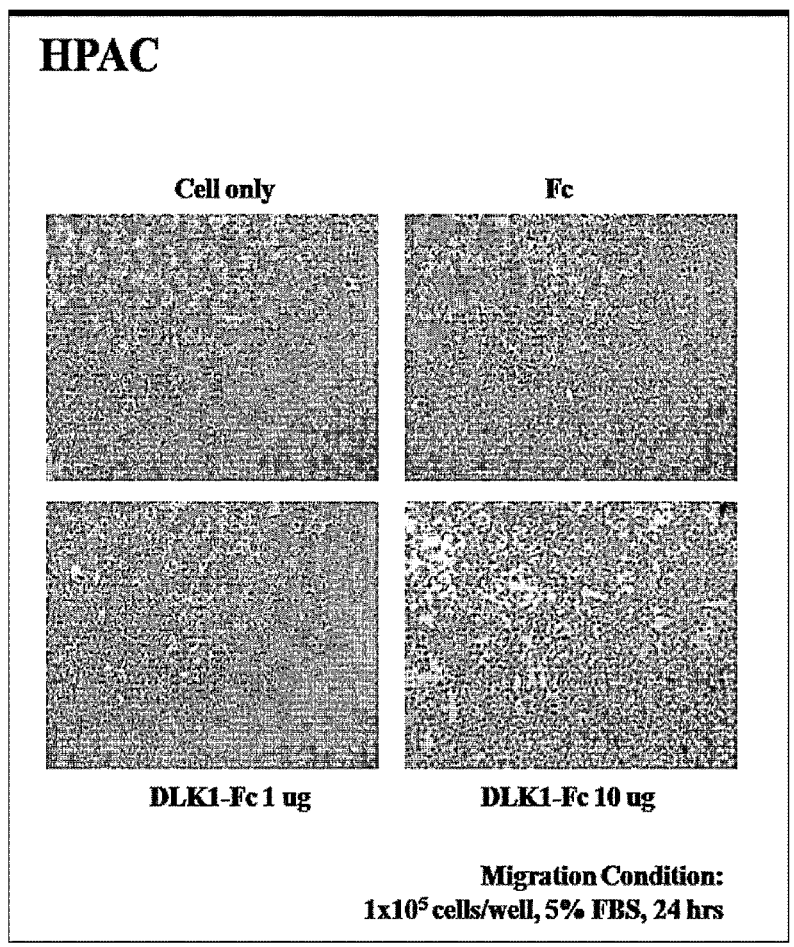
FIG. 30 shows the migration inhibition effect of the cell culture medium containing soluble DLK1-Fc fusion protein in pancreatic cancer cell line (HPAC).
Figure 31:
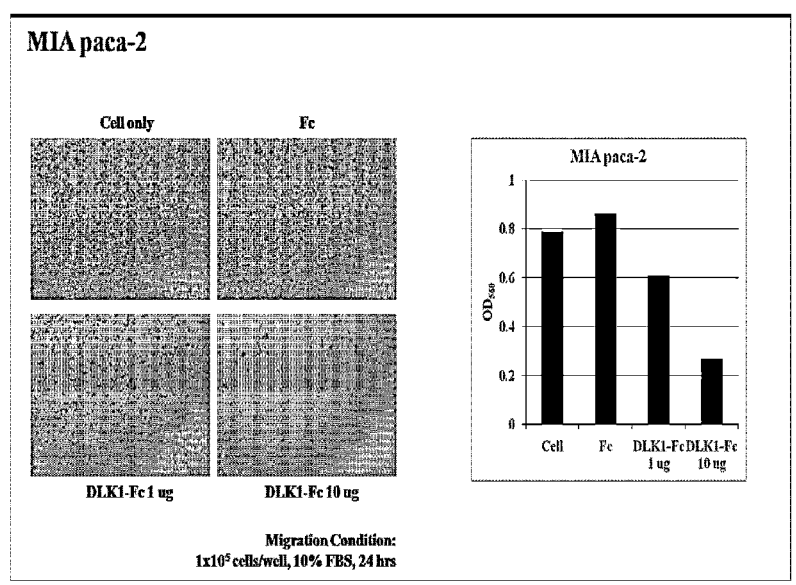
FIG. 31 shows the migration inhibition effect of the cell culture medium containing soluble DLK1-Fc fusion protein in pancreatic cancer cell line (MIA paca-2).
Figure 32:
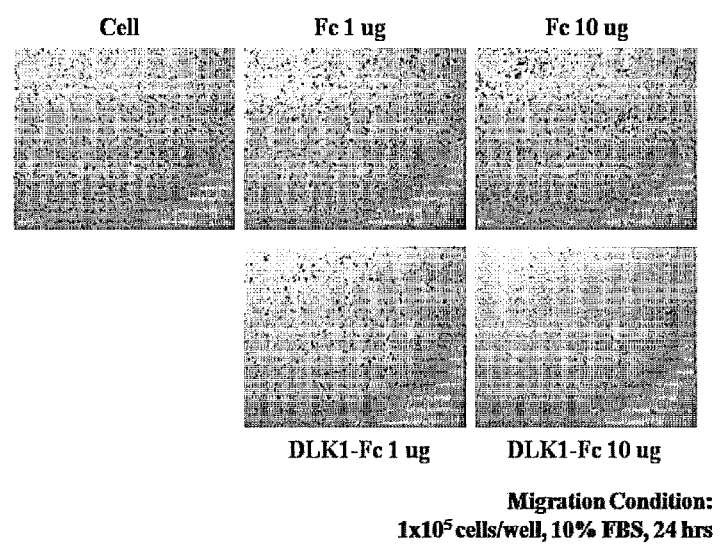
FIG. 32 shows the migration inhibition effect of the cell culture medium containing soluble DLK1-Fc fusion protein in stomach cancer cell line (SNU638).
Figure 33:
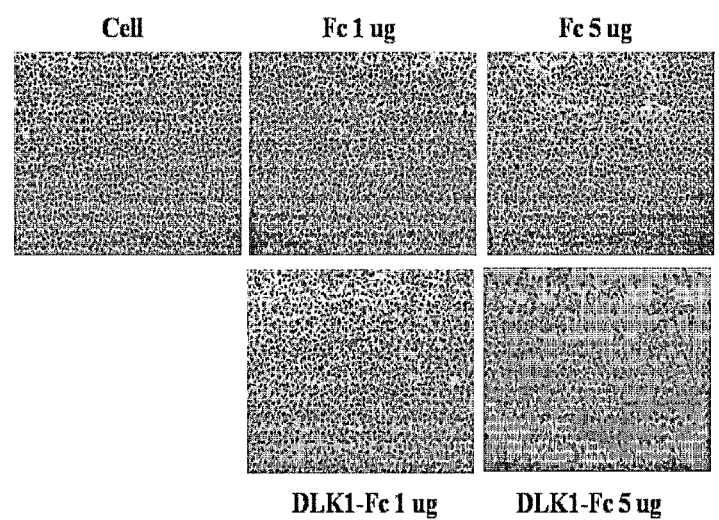
FIG. 33 shows the migration inhibition effect of the cell culture medium containing soluble DLK1-Fc fusion protein in stomach cancer cell line (AGS).

In a particular example of the present invention, the influence of the prepared DLK1-Fc fusion protein on cancer cell line was analyzed. That is, using the method of Chen H C, *Methods in molecular biology.* 294:15-22, 2005, incorporated herein as a reference, cancer cell line migration assay was conducted. Also, as a result of studying influence of the purified DLK1-Fc fusion protein on metastasis of various cancer cells, it was confirmed that DLK1-Fc fusion protein can reduce metastasis of skin cancer (FIG. 11), breast cancer (FIGS. 14 and 15), uterine cancer (FIG. 16), colon cancer (FIGS. 17 and 18), kidney cancer (FIGS. 19 and 20), liver cancer (FIGS. 21 to 23), lung cancer (FIGS. 24 to 26), ovarian cancer (FIGS. 27 and 28), pancreatic cancer (FIGS. 29 to 31) and stomach cancer (FIGS. 32 and 33).

Figure 12:
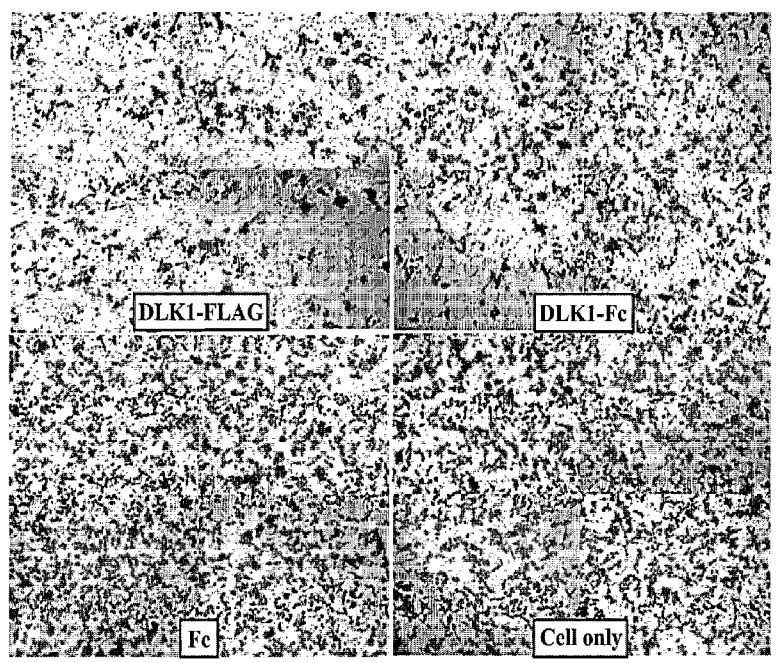
FIG. 12 shows the migration inhibition effect of the cell culture medium containing the extracellular soluble domain of DLK1 and soluble DLK1-Fc fusion protein in skin cancer melanoma line (MDA-MB-435), where:
sDLK1, sDLK1-Fc, and Fc are used in 10 ug/ml, respectively.
Figure 13:
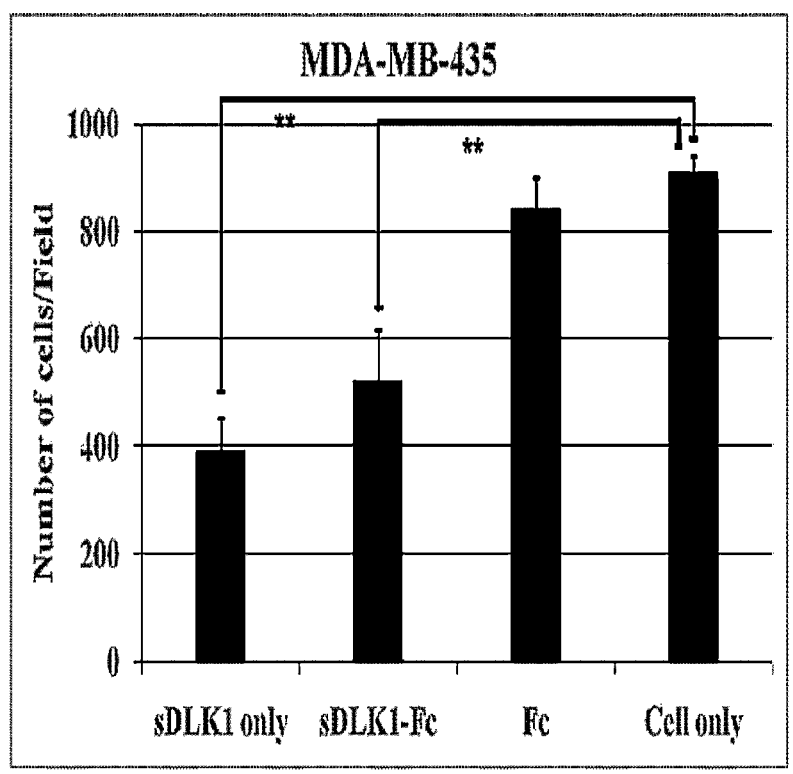
FIG. 13 is a graph showing the migration inhibition effect of the cell culture medium containing the extracellular soluble domain of DLK1 and soluble DLK1-Fc fusion protein in skin cancer melanoma line (MDA-MB-435), where:
sDLK1, sDLK1-Fc, and Fc are used in 10 ug/ml, respectively.

Further, the prepared extracellular soluble domain of DLK1 was selectively expressed and purified, and treated with skin cancer melanoma. Then as a result of comparing, it was confirmed that the extracellular soluble domain of DLK1 can also markedly decrease migration of cancer cell (FIGS. 12 and 13).

Figure 35:
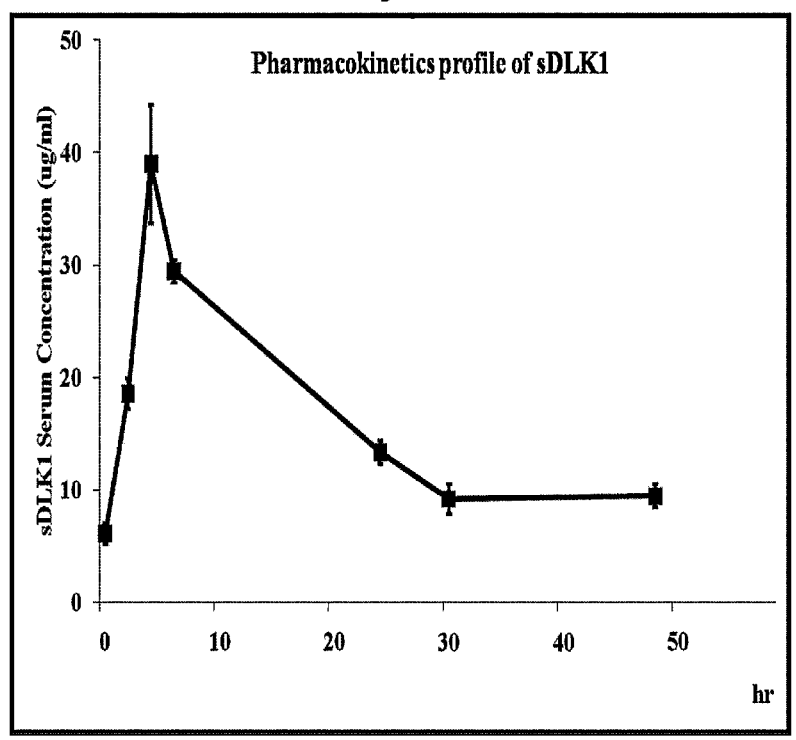
FIG. 35 shows the result of pharmacokinetic test of soluble DLK1-Fc fusion protein.

Additionally, in order to investigate efficacy as a drug for inhibiting cancer metastasis, experiment for determining pharmacokinetic parameters was conducted on mouse. Considering that the experiment injected 5 mg/kg (i.e., 100 ug/mouse, considering the actual weight of the mouse), and the total blood of the mouse was approximately 2 ml, the maximum concentration that can be estimated by the intravenous injection was 50 ug/ml. Accordingly, 38.96 ug/ml (Cmax) as the result of experimenting by peritoneal injection is considerably high value. It was confirmed that the maximum concentration appears 4 hours after the injection (Tmax). As for the half-life, which represents how the drug can remain stable in vivo, it was approximately 20 hours, thereby confirming that the drug is considerably stable in vivo (see FIG. 36). Since the concentration representing the metastasis inhibition force was very good at concentration of 10 ug/ml, in view of the fact that the concentration approximately of 10 ug/ml was maintained after 48 hours, it is apparent that the drug provides sufficient safety and efficacy as a new drug to inhibit cancer metastasis (FIG. 35).

Accordingly, the soluble domain in the extracellular DLK1 domain, or DLK1-Fc fusion protein prepared as explained above can be efficaciously used as an effective ingredient of a composition for inhibiting cancer metastasis.

The composition according to the present invention may additionally include one or more type of effective ingredient with the same or similar function. For administration, the composition may additionally include one or more type of pharmaceutically-acceptable carrier. The composition according to the present invention includes 0.0001 to 10 wt. %, or preferably 0.001 to 1 wt. % of protein with respect to the total weight of the composition. The pharmaceutically-acceptable carrier may include saline solution, distilled water, Ringer's solution, buffer saline solution, dextrose solution, maltodextrin solution, glycerol, ethanol and a mixture of one or more thereof, and as need arises, additionally include other conventional additives such as antioxidant, buffer solution, bacteristat, or the like. The composition may also be prepared into dosage form for injection such as aqueous solution, suspension, or emulsion, tablet, capsule, powder or pill by additionally including diluents, dispersant, suffactant, binder and lubricant. Further, the composition may be formulated into a desirable form depending on targeting disease or ingredients thereof, using the method disclosed in Remington's Pharmaceutical Science (Mack Publishing Company, Easton Pa., 18th, 1990).

The composition for inhibiting cancer metastasis according to the present invention may be administered by perenteral administration (e.g., intravenous, intramuscular, intra-abdominal, subcutaneous or topical administration), or oral administration, with dosage varying in wide range depending on the weight, age, gender, health condition, diet, time of administration, method of administration, excretion rate, and severity of disease of the patient. For an adult male who is 60 kg in weight, the amount of protein to be administered ranges between 0.738 ug~7.38 g (based on the FDA standard, U.S.A), preferably, 7.38 ug~0.738 g (12.3 mpk), and it is desirable to administer the protein once in every second day, but this can be determined according to the need of a patient.

Further, the present invention provides a method for inhibiting cancer metastasis, comprising the step of administering a pharmaceutically-effective amount of the extracellular soluble domain of DLK1 or DLK1-Fc fusion protein prepared as explained above into a subject with metastatic tumor.

The extracellular soluble domain of DLK1 may preferably have an amino acid sequence of SEQ. ID. No. 4, but not limited thereto.

The term "DLK1-Fc fusion protein" herein refers to a recombinant molecule containing a fraction derived from a heavy chain constant domain. The Fc-fusion protein may include all, or part of CH2 and CH3 constant domains, such as Fc domain of an antibody randomly selected from the five Ig types (e.g., IgA, may be administered by parenteral injection (e.g., intravenous, intramuscular, intra-abdominal, subcutaneous or topical administration), and the dosage varies in wide range depending on the weight, age, gender, health condition, diet, time of administration, method of administration, excretion rate and severity of disease of the patient. According to the present invention, the protein may be administered to, for example an adult male who is 60 kg in weight (based on FDA standard, USA), in amount ranging between 0.738 ug~7.38 g, and preferably, 7.38 ug~0.738 g (12.3 mpk), and it is preferable to administer once in every second day, but the method of administration may vary depending on a need of a patient.

The present invention constructs a recombinant expression vector comprising extracellular soluble domain gene of DLK1 with the gene of Fc domain of IgG antibody, expresses and purifies DLK1-Fc fusion protein from 293E cell, and confirms noticeable reduction of migration by DLK1-Fc fusion protein and also the efficacy as a drug to inhibit cancer metasis based on computation of pharmacokinetic parameters. As a result, administering the extracellular soluble domain of DLK1 or the DLK1-Fc fusion protein into a subject with metastatic tumor, can be effectively used in the method for inhibiting cancer metastasis.

Further, the present invention provides a use of the extracellular soluble domain of DLK1 or DLK1-Fc fusion protein prepared as explained above, for preparation of a composition for inhibiting cancer metastasis.

The extracellular soluble domain of DLK1 may preferably have an amino acid sequence of SEQ. ID. No. 4, but not limited thereto.

The term "DLK1-Fc fusion protein" herein refers to a recombinant molecule containing a fraction derived from a heavy chain constant domain. The Fc-fusion protein may include all or part of CH2 and CH3 constant domains, such as Fc domain of an antibody randomly selected from the five Ig types (e.g., IgA, IgD, IgE, IgG and IgM). By way of example, the DLK1-Fc fusion protein may be formed into a pattern that includes all or part of the heavy chain constant domains of an antibody at carboxy- and amino-terminals of the extracellular soluble domain. As another example, the Fc fusion protein may also include a pattern having heavy chain constant domains of two or more antibodies, in which two heavy chains may be connected by desulfided or covalent bond. As yet another example, the DLK1 part of the Fc fusion protein may also include a pattern having two or more extracellular soluble domains of DLK1.

The cancer may be one selected from a group consisting of skin cancer, liver cancer, stomach cancer, breast cancer, colon cancer, cancer of a bone, pancreatic cancer, head cancer or neck cancer, uterine cancer, colon cancer, lung cancer, ovarian cancer, cancer of rectum, cancer of esophagus, cancer of small bowel, anal cancer, colon cancer, cancer of fallopian tube, endometrial carcinoma, cervical carcinoma, vaginal cancer, vulva cancer, Hodgkin's disease, prostate cancer, bladder cancer, kidney cancer, ureteral cancer, renal cell carcinoma, renal pelvic carcinoma, and tumors of central nervous system, and more preferably, one selected from a group consisting of skin cancer, breast cancer, uterine cancer, colon cancer, kidney cancer, liver cancer, lung cancer, ovarian cancer, stomach cancer, and pancreatic cancer, but not limited thereto.

The present invention constructs a recombinant expression vector comprising extracellular soluble domain gene of DLK1 with the gene of Fc domain of IgG antibody, expresses and purifies DLK1-Fc fusion protein from 293E cell, and confirms noticeable reduction of migration by DLK1-Fc fusion protein and also the efficacy as a drug to inhibit cancer metasis based on computation of pharmacokinetic parameters. As a result, administering the extracellular soluble domain of DLK1 or the DLK1-Fc fusion protein into a subject with metastatic tumor, can be effectively used in the method for inhibiting cancer metastasis.

The composition according to the present invention may additionally include one or more type of effective ingredient with the same or similar function. For administration, the composition may additionally include one or more type of pharmaceutically-acceptable carrier. The composition according to the present invention includes 0.0001 to 10 wt. %, or preferably 0.001 to 1 wt. % of protein with respect to the total weight of the composition. The pharmaceutically-acceptable carrier may include saline solution, distilled water, Ringer's solution, buffer saline solution, dextrose solution, maltodextrin solution, glycerol, ethanol and a mixture of one or more thereof, and as need arises, additionally include other conventional additives such as antioxidant, buffer solution, bacteristat, or the like. The composition may also be prepared into dosage form for injection such as aqueous solution, suspension, or emulsion, tablet, capsule, powder or pill by additionally including diluents, dispersant, suffactant, binder and lubricant. Further, the composition may be formulated into a desirable form depending on targeting disease or ingredients thereof, using the method disclosed in Remington's Pharmaceutical Science (Mack Publishing Company, Easton Pa., 18th, 1990).

The composition for inhibiting cancer metastasis according to the present invention may be administered by perenteral administration (e.g., intravenous, intramuscular, intra-abdominal, subcutaneous or topical administration), or oral administration, with dosage varying in wide range depending on the weight, age, gender, health condition, diet, time of administration, method of administration, excretion rate, and severity of disease of the patient. For an adult male who is 60 kg in weight, the amount of protein to be administered ranges between 0.738 ug~7.38 g (based on the FDA standard, U.S.A), preferably, 7.38 ug~0.738 g (12.3 mpk), and it is desirable to administer the protein once in every second day, but this can be determined according to the need of a patient.

Several embodiments, experimental examples and preparation examples according to the present invention will be explained in greater detail below.

However, it should be noted that the embodiments, experimental examples and preparation examples described herein are only written for illustrative purpose, and accordingly, should not be construed as limiting.

Example 1

Preparation of pYK602-his-DLK1 Expression Vector

To induce DLK1-Fc expression of pYK602-HIS vector, a pair of primers represented as SEQ ID NO. 2 (5'-CAGGGGGCCGTGGGGGCCGAATGCTTC-CCGGCCTGCAA-3') and SEQ ID NO. 3 (5'-TAGCGGC-CGACGCGGCCGCCCTCGGTGAGGAGAGGGG-3'), respectively, was prepared and then polymerase chain reaction (PCR) was performed. The specific reaction combination was as follows: 100 ng of DNA library mix (a mixture of kidney, placenta, pancreas, and liver) which was used as a template and 10 pmol of each pfu 2.5 unit primer were added, and allowed to react in 50 ul in total. The reaction was conducted at 94° C., 2 minutes for 1 cycle, 94° C., 30 seconds, 55° C., 30 seconds, 72° C., 1 minute for 30 cycles, and 72° C., 10 minutes for 1 cycle, and completed. Since the resultant of PCR includes SfiI restriction enzyme site, restriction enzyme reaction was conducted with SfiI, and then inserted into pYK602-HIS vector to render pYK602-His-DLK1 recombinant vector (FIG. 5).

Cloned DLK1 is the extracellular soluble domain of DLK1 which corresponds from 25th to 302th amino acids among the total 383 amino acids, from which signal peptide, transmembrane region and cytoplasmic domain are removed. Nucleic acid sequence and amino acid sequence of the cloned DLK1 is shown in FIG. 6 (SEQ ID NO: 1) and FIG. 7 (SEQ ID NO: 4), respectively.

Example 2

Expression and Purification of DLK1-Fc Fusion Protein

To express the DLK1-Fc cloned at Example 1, 293E cell was used. The specific method of expression is as follows. In 100 mm of plate, with approximately 70% level of cells, 10 ug of DNA and 20 ug of PEI (#23966, Polysciences, USA) were mixed, reacted for 20 minutes at a room temperature to render a mixture, and then treated with cell. After 16~10 hours, free-serum DMEM culture medium was replaced, and once in every second day, the culture medium was recovered and replaced with new culture medium. Expression of the recovered culture medium was confirmed by Western blotting (FIG. 8). The culture medium with the IgD, IgE, IgG and IgM). By way of example, the DLK1-Fc fusion protein may be formed into a pattern that includes all or part of the heavy chain constant domains of an antibody at carboxy- and amino-terminals of the extracellular soluble domain. As another example, the Fc fusion protein may also include a pattern having heavy chain constant domains of two or more antibodies, in which two heavy chains may be connected by desulfided or covalent bond. As yet another example, the DLK1 part of the Fc fusion protein may also include a pattern having two or more extracellular soluble domains of DLK1.

The cancer may be one selected from a group consisting of skin cancer, liver cancer, stomach cancer, breast cancer, colon cancer, cancer of a bone, pancreatic cancer, head cancer or neck cancer, uterine cancer, colon cancer, lung cancer, ovarian cancer, cancer of rectum, cancer of esophagus, cancer of small bowel, anal cancer, colon cancer, cancer of fallopian tube, endometrial carcinoma, cervical carcinoma, vaginal cancer, vulva cancer, Hodgkin's disease, prostate cancer, bladder cancer, kidney cancer, ureteral cancer, renal cell carcinoma, renal pelvic carcinoma, and tumors of central nervous system, and more preferably, one selected from a group consisting of skin cancer, breast cancer, uterine cancer, colon cancer, kidney cancer, liver cancer, lung cancer, ovarian cancer, stomach cancer, and pancreatic cancer, but not limited thereto.

Depending on the purpose of use, the method for inhibiting cancer metastasis according to the present invention confirmed expression was centrifuged to remove possibly-remaining cells, and filtered through 0.22 um of filter (#PR02890 Millipore, USA). After that, purification was performed by using protein A column. That is, in 10 ml of column, 500 ul of protein A beads (#17-1279-03 GE, Sweden) was filled, washed with PBS, and culture medium with DLK1-Fc expression was flowed. In this process, peristartic pump was used, which was set to allow the flow of 0.5 ml per minute. When the culture medium completely went through the column, the culture medium was washed with PBS, and DLK1-Fc protein purified with 0.1 M glycine-HCl (#G7126, Sigma, USA) was recovered. The pH of recovered protein was neutralized by using 1M Tris pH 9.0(#T-1503, Sigma, USA), and then by using PBS, dialysis was conducted. By BCA analysis, the quantification of the purified protein was performed, and SDS-PAGE was performed to confirm the purification (FIG. 9) to obtain purified DLK1-Fc fusion protein.

Experimental Example 1

Measurement and Removal of Endotoxin of Purified DLK1-Fc

Chromo-LAL(cat# C0031, CAPE COD) was used to measure the data of bacterial endotoxin of the purified DLK1-Fc. To be specific, 1 EU/ml of CSE (control standard endotoxin; cat# E0005, CAPE COD) as the protein standard substance was diluted two times to achieve concentration of 0.03125 EU/ml. LRW (LAL reagent water; cat# WP1001, CAPE COD) (100 ul+LAL 100 ul) as a negative control, and standard (100 ul+LAL 100 ul) as a positive control in concentration of 0.125 EU/ml were added. For analysis, 100 ul+LAL 100 ul of diluted LRW sample, which has a predetermined concentration (50 ug/ml), was prepared. Additionally, to check interference between the samples, the above-mentioned diluted sample (50 ul+0.125 EU/ml) and standard (50 ul+LAL 100 ul) were also prepared for the experiment of product positive control. Further, a file (Chromo LAL setting.pda), which is the protocol data of a preset value, was used for the measurement of VersaMax microplate reader (Molecular devices). The plate was pre-warmed at 37° C. for about 10 minutes before the experiment. LAL was processed, and at the same time, the absorbance was measured, starting from the set file. Standard curve was constructed using Log EU/mL as X axis, and Log Onset time as Y axis, and the absorbance measuring the endotoxin data of the sample was automatically computed on a software and expressed in EU/ml unit. Reliability of the measurements was determined when $R^2$ of the standard curve exceeds 0.98. As a result of LAL test on DLK1-Fc protein, 150.24 EU/ml of endotoxin was measured. Next, EndoTrap Red (cat#83-009U, Lonza) column was used to remove endotoxin of the sample. The column was rinsed with 3 ml of refresh buffer two times, and rinsed with the same amount of stabilization buffer two times. Next, the sample was applied, and at the same time, fraction was received (rate: 0.5~1 ml/minute). Remaining sample inside the column was received by applying 1 ml of stabilization buffer. After endotoxin removal, LAL test was re-conducted in the same manner as explained above, and as a result, 7.53 EU/ml of endotoxin data was measured, which is similar amount to that of the negative control. Accordingly, it was confirmed that the bacterial endotoxin of the purified DLK1-Fc protein was removed.

Experimental Example 2

Confirmation of Inhibition Effect of DLK1-Fc Fusion Protein Against Migration of Cancer Cell Line The migration assay of cancer cell line was conducted using the method of Chen H C, Methods in molecular biology. 294:15-22, 2005 to investigate influence of the DLK1-Fc protein prepared and purified in <Example 2>.

Figure 21:
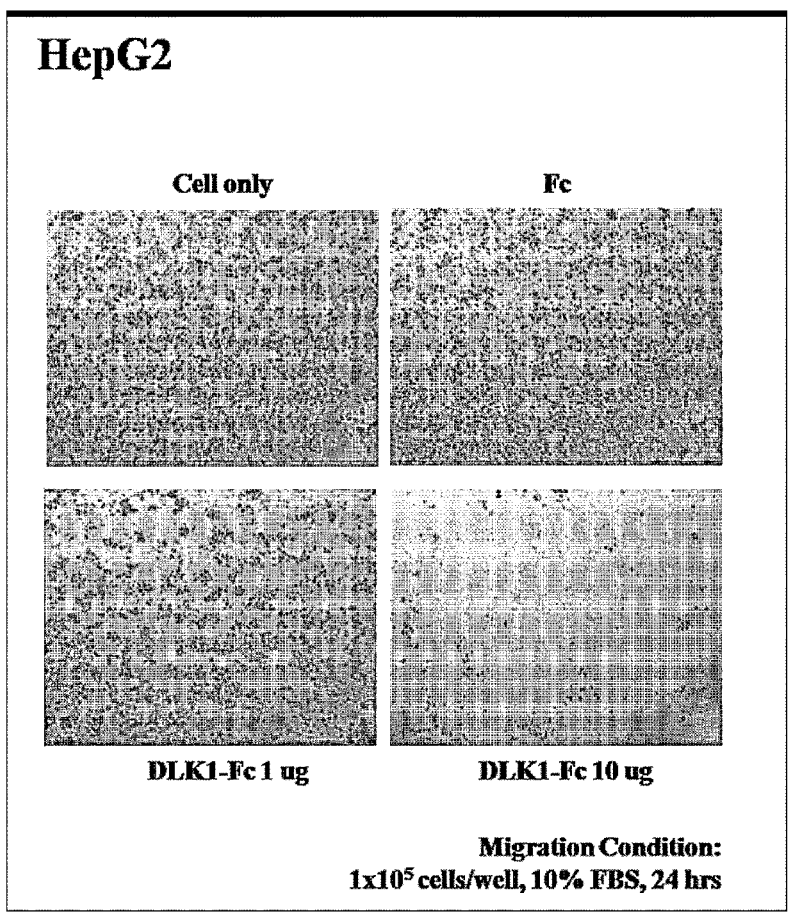
FIG. 21 shows the migration inhibition effect of the cell culture medium containing soluble DLK1-Fc fusion protein in liver cancer cell line (HepG2).

To be specific, cancer cell lines [skin cancer cell line (MDA-MB-435; ATCC HTB-129), breast cancer cell line (Hs578T; ECACC 86082104 and MCF-7; ATCC HTB-22), uterine cancer cell line (HeLa; ATCC CCL-2), colon cancer cell line (SW480; ATCC CCL-228, SW620; ATCC CCL-227 and HT29; ATCC HTB-38), kidney cancer cell line (786-O; ATCC CRL-1932 and UO-31; DTP), liver cancer cell line (HepG2; ATCC HB-8065, SNU398; KCLB 00398 and SNU449; KCLB 00449), lung cancer cell line (A549; ATCC CCL-185, NCIH23; KCLB 90023 and NCIH460; KCLB 30177), ovarian cancer cell line (MDAH2774; ATCC CRL-10303 and IGROV-1; DTP), pancreatic cancer cell line (Aspc-1; KCLB 21682, HPAC; ATCC CRL-2119 and MIA paca-2; KCLB 21420) and stomach cancer cell line (SNU638; KCLB 00638 and, AGS; KCLB 21739)] were cultured, replaced with free-serum medium when level of cells was approximately 50%, cells were removed after 24 hours by trypsin and the number of cells was measured. The cells, free-serum medium and respective proteins to be treated were mixed together to a 100 ul of mixture and incubated at 37° C. for 1 hour. 1 ml of chemo-attractant was placed in 24-well plate, trans well (Corning #3422) having 8.0 um pores was placed thereon, and 100 ul of the pre-cultured mixture of cells, cells, and protein was placed therein, and incubated in 37° C. carbon dioxide culture medium from 24 to 48 hours. FIG. 21 shows the number of cells, constitution of chemical attractant, and time of culture used with respect to the respective cell lines.

After culturing, the medium of the trans well was removed, and fixed for 15 minutes in 100% methanol, and after that, rinsed two times using distilled water, and reacted for 5 minutes in crystal violet solution. After the reaction, the mixture was rinsed three times by distilled water, and the cells that have not passed the trans well were removed completely using cotton swab. After the trans well was dried completely, the cells passed through the trans well were observed by observation and photography with 100 magnification. For quantification analysis, 10% acetic acid was placed in the trans well after the photographing and extracted, measurement was made at 560 nm wavelength to analyze the absorbance.

Figure 10:
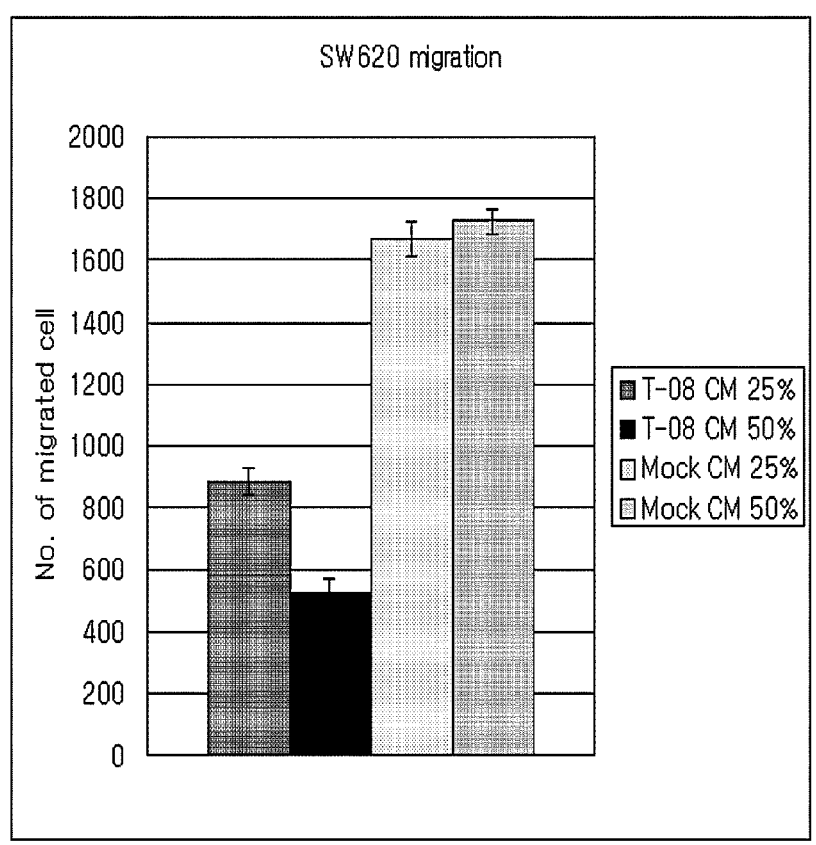
FIG. 10 shows the migration inhibition effect of the cell culture medium containing DLK1-Fc fusion protein in colon cancer cell line (SW620).
Figure 11:
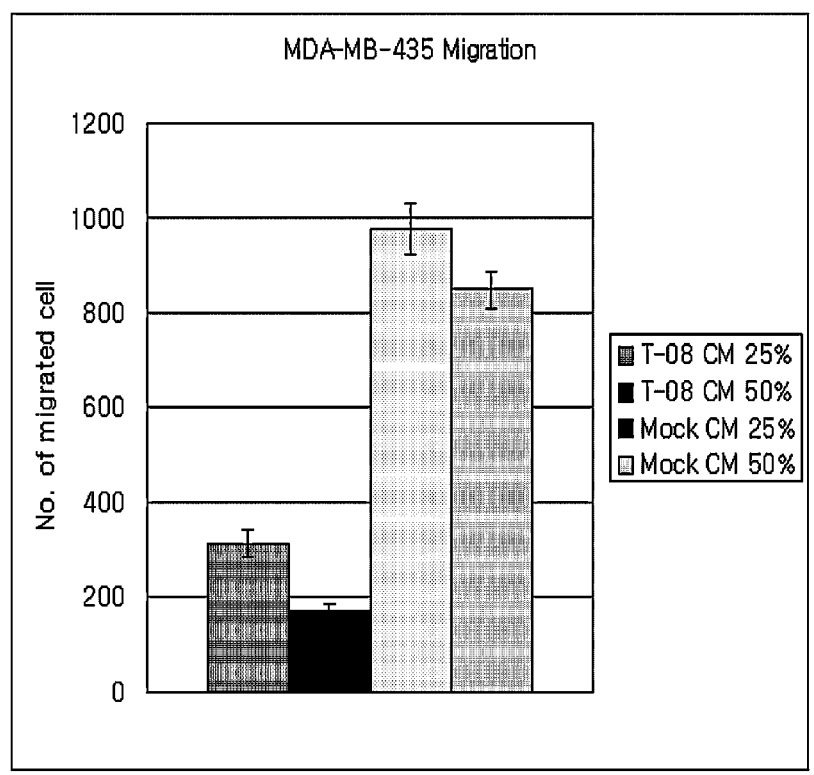
FIG. 11 shows the migration inhibition effect of the cell culture medium containing DLK1-Fc fusion protein in skin cancer melanoma line (MDA-MB-435).

As a result, the colon cancer cell line (SW620) and skin cancer melanoma cell line (MDA-MB-435), treated with the cell medium containing soluble DLK1-Fc fusion protein, exhibited markedly increased inhibition of the migration of cancer cell lines by the soluble DLK1-Fc fusion protein, compared to a control soluble Fc protein and non-treated group (FIGS. 10 and 11). Further, the soluble region of DLK1 was selectively expressed and purified to confirm that the migration was due to the influence of Fc binding to DLK1, and as a result, markedly increased inhibition of cancer cell line was confirmed as in the case of the soluble DLK1-Fc fusion protein (FIGS. 12 and 13). The influence of the purified soluble DLK1 Fc fusion protein on the metastasis of various cancer cell lines was also studied, and as a result, migration inhibition effect against breast cancer (FIGS. 14 and 15), uterine cancer (FIG. 16), colon cancer (FIGS. 17 and 18), kidney cancer (FIGS. 19 and 20), liver cancer (FIGS. 21 to 23), lung cancer (FIGS. 24 to 26), ovarian cancer (FIGS. 27 and 28), pancreatic cancer (FIGS. 29 내지 31) and stomach cancer (FIGS. 32 and 33) was confirmed.

Experimental Example 3

Confirmation of Pharmacokinetic Parameter of DLK1-Fc Fusion Protein

Pharmacokinetic test was conducted to investigate applicability of the DLK1-Fc fusion protein, prepared and purified as explained in <Example 2>, for use as a cancer metastasis inhibitor.

To be specific, 5 mg/kg was injected once by abdominal injection to 30 6-week-old female Balb/c (Orient Bio), blood was taken from ophtalmic venus plexus at 0, 0.5, 2, 4, 6, 24, 30, 48 hours, and serum was separated and used in the test.

Enzyme-linked immunosorbent assay (ELISA) was used to measure the DLK1-Fc blood concentration using the sampled serum. To be specific, DLK1 antibody (#MAB1144, R&D) in concentration of 1 ug/ml was coated on the ELIZA plate (#439454, NUNC) at 4° C. Blocking was conducted for 1 hour with 4% skim milk/PBS (potassium phosphate saline) buffer, and the plate was rinsed with PBST (potassium phosphate saline, 0.05% Tween 20) buffer. To construct a standard curve, the purified DLK1-Fc was diluted from 100 nM concentration two times. hIgG (human IgG) was used as a negative control. The serum sampled in the test was diluted by 250 times, 500 times, and 1000 times, respectively, and reacted at a room temperature for 2 hours. The plate was rinsed with the PBT buffer, and anti Fc-HRP(#31413, Pierce) antibody was diluted in 1:4000 concentration and reacted at a room temperature for 2 hours. The plate was rinsed with the PBST buffer, and OPD(o-Phenylenediamine dihydrochloride) solution was prepared. The respective wells were treated with 100 ul of OPD solution. The OPD solution was prepared by adding to PC buffer, pH 5.0, oxygenated water and OPD(P9187, Sigma). After reaction in dark room for 10 minutes, the wells were treated with 50 ul of 2.5 M sulfuric acid. Accordingly, color reaction was completed and absorbence was measured at OD 492 nm. The region where $R^2$ exceeds 0.99 was selected and the result was processed for the standard curve.

As a result, considering that 5 mg/kg (100 ug/mouse, considering the actual weight of the mouse) was injected and the total blood of the mouse is approximately 2 ml, the maximum concentration that can be estimated was 50 ug/ml, and the test result by the abdominal injection showed considerably high concentration, i.e., Cmax v=38.96 ug/ml. Accordingly, the maximum concentration appears 4 hours after the injection (Tmax). As for the half-life, which represents how the drug can remain stable in vivo, it was approximately 20 hours, thereby confirming that the drug is considerably stable in vivo (see FIG. 36). Since the concentration representing the metastasis inhibition force was very good at concentration of 10 ug/ml, in view of the fact that the concentration approximately of 10 ug/ml was maintained after 48 hours, it is apparent that the drug provides sufficient safety and efficacy as a new drug to inhibit cancer metastasis (FIG. 35).

Accordingly, considering that the DLK1-Fc fusion protein can inhibit migration of various tumors and also considering the pharmacokinetic parameters, it is apparent that the DLK1-

Fc fusion protein provides sufficient probability as a composition for inhibiting cancer metastasis.

Examples of preparing the composition according to the present invention will be explained below.

Preparation Example 1

Pharmaceutical Preparation

1. Preparation of Powders

| DLK1-Fc fusion protein | 2 g |
|---|---|
| Lactose | 1 g |

The above ingredients were mixed, and filled in airtight sachet to render powders.

2. Preparation of Tablets

| DLK1-Fc fusion protein | 100 mg |
|---|---|
| Corn starch | 100 mg |
| Lactose | 100 mg |
| Magnesium stearate | 2 mg |

The above ingredients were mixed and packed into tablets according to a general conventional tablet packing method.

3. Preparation of Capsules

| DLK1-Fc fusion protein | 100 mg |
|---|---|
| Corn starch | 100 mg |
| Lactose | 100 mg |
| Magnesium stearate | 2 mg |

The above ingredients were mixed and filled in gelatin capsules according to a general conventional capsule preparation method.

5. Preparation of Injection

| DLK1-Fc fusion protein | 10 μg/Ml |
|---|---|
| Hydrochloric acid BP | until pH 7.6 |
| Sodium chloride for injection BP | maximum 1 Ml |

DLK1-Fc fusion protein was dissolved in appropriate. sodium nitride for injection BP content, pH of the generated solution was regulated to pH 7.6 using hydrochloric acid BP, the content was regulated using sodium nitride for injection BP, and the solution was mixed sufficiently. The solution was filled in 5 ml type I ampoule of transparent glass, the glass was melt, and the solution was sealed under gas. The ampoule was autoclaved for more than 15 minutes at 120° C. to render injection.

6. Preparation of Pills

| DLK1-Fc fusion protein | 1 g |
|---|---|
| Lactose | 1.5 g |
| Glycerin | 1 g |
| Xylitol | 0.5 g |

The above ingredients were mixed and prepared into 4 g of pill according to a general conventional method.

7. Preparation of Granule

| DLK1-Fc fusion protein | 150 mg |
|---|---|
| Soybean extract | 50 mg |
| Glucose | 200 mg |
| Starch | 600 mg |

The above ingredients were mixed, and 100 mg of 30% ethanol was added, dried at 60° C. to render granules and packed in sachet.

INDUSTRIAL APPLICABILITY

The DLK1-Fc fusion protein has a higher stability compared to non-fusion protein, significantly reduces migration of various cancer cell lines, and provides markedly increased cancer migration even at a small concentration. Accordingly, the DLK1-Fc fusion protein can be used efficaciously as a composition for inhibiting cancer metastasis, and preventing and treating cancer, and as a composition of health food for preventing and improving cancer. Furthermore, when commercialized for use in combination with an anti-angiogenesis composition which is currently available as a cancer treatment, the DLK1-Fc fusion protein can be efficaciously used as a composition for inhibiting cancer metastasis and treating cancer with significantly increased anti-cancer activity.

The invention claimed is:

1. A method for inhibiting cancer metastasis, comprising: administering a pharmaceutically effective amount of the extracellular soluble domain of delta-like 1 homolog (DLK1) or a DLK1-Fc fusion protein comprising the extracellular soluble domain of DLK1 and a human antibody Fc domain to a subject with a metastatic cancer, wherein the extracellular soluble domain of DLK1 consists of the amino acid sequence of SEQ ID NO:4.

2. The method according to claim 1, wherein the cancer is selected from the group consisting of skin cancer, breast cancer, uterine cancer, colon cancer, kidney cancer, liver cancer, lung cancer, ovarian cancer, pancreatic cancer and stomach cancer.

3. The method according to claim 1, wherein the DLK1-Fc fusion protein is prepared by a method comprising:
   i) preparing a recombinant vector containing a polynucleotide coding the DLK1-Fc fusion protein comprising the extracellular soluble domain of DLK1 consisting of the amino acid sequence of SEQ ID NO:4 and a human antibody Fc domain;
   ii) preparing a recombinant cell line in which the recombinant vector is transfected into a host cell;
   iii) culturing the recombinant cell line; and
   iv) separating the DLK1-Fc fusion protein from the recombinant cell line culture.

4. The method according to claim 1, wherein the extracellular soluble domain of delta-like 1 homolog (DLK1) or a DLK1-Fc fusion protein comprising the extracellular soluble domain of DLK1 and a human antibody Fc domain inhibits the migration of cancer cells.

5. The method according to claim 4, wherein the cancer cell is selected from the group consisting of skin cancer cell, breast cancer cell, uterine cancer cell, colon cancer cell, kidney cancer cell, liver cancer cell, lung cancer cell, ovarian cancer cell, pancreatic cancer cell and stomach cancer cell.

* * * * *

SEQUENCE LISTING

```
<160> NUMBER OF SEQ ID NOS: 4

<210> SEQ ID NO 1
<211> LENGTH: 834
<212> TYPE: DNA
<213> ORGANISM: Homo sapiens

<400> SEQUENCE: 1
gaatgcttcc cggcctgcaa cccccaaaat ggattctgcg aggatgacaa tgtttgcagg      60
tgccagcctg gctggcaggg tccccttgt gaccagtgcg tgacctctcc cggctgcctt     120
```

```
cacggactct gtggagaacc cgggcagtgc atttgcaccg acggctggga cggggagctc      180
tgtgatagag atgttcgggc ctgctcctcg gccccctgtg ccaacaacgg gacctgcgtg      240
agcctggacg atggcctcta tgaatgctcc tgtgcccccg ggtactcggg aaaggactgc      300
cagaaaaagg acgggccctg tgtgatcaac ggctccccct gccagcacgg aggcacctgc      360
gtggatgatg agggccgggc ctcccatgcc tcctgcctgt gcccccctgg cttctcaggc      420
aatttctgcg agatcgtggc caacagctgc acccccaacc catgcgagaa cgacggcgtc      480
tgcactgaca ttgggggcga cttccgctgc cggtgcccag ccggcttcat cgacaagacc      540
tgcagccgcc cggtgaccaa ctgcgccagc agcccgtgcc agaacggggg cacctgcctg      600
cagcacaccc aggtgagcta cgagtgtctg tgcaagcccg agttcacagg tctcacctgt      660
gtcaagaagc gcgcgctgag cccccagcag gtcacccgtc tgcccagcgg ctatgggctg      720
gcctaccgcc tgacccctgg ggtgcacgag ctgccggtgc agcagccgga gcaccgcatc      780
ctgaaggtgt ccatgaaaga gctcaacaag aaaaccccctc tcctcaccga gggc           834

<210> SEQ ID NO 2
<211> LENGTH: 38
<212> TYPE: DNA
<213> ORGANISM: Artificial Sequence
<220> FEATURE:
<223> OTHER INFORMATION: Forward primer for DLK1(delta-like 1 homolog)

<400> SEQUENCE: 2 caggggggccg tgggggccga atgcttcccg gcctgcaa                              38

<210> SEQ ID NO 3
<211> LENGTH: 37
<212> TYPE: DNA
<213> ORGANISM: Artificial Sequence
<220> FEATURE:
<223> OTHER INFORMATION: Reverse primer for DLK1(delta-like 1 homolog)

<400> SEQUENCE: 3
tagcggccga cgcggccgcc ctcggtgagg agagggg                                37

<210> SEQ ID NO 4
<211> LENGTH: 278
<212> TYPE: PRT
<213> ORGANISM: Homo sapiens

<400> SEQUENCE: 4

Glu Cys Phe Pro Ala Cys Asn Pro Gln Asn Gly Phe Cys Glu Asp Asp
1               5                   10                  15

Asn Val Cys Arg Cys Gln Pro Gly Trp Gln Gly Pro Leu Cys Asp Gln
            20                  25                  30

Cys Val Thr Ser Pro Gly Cys Leu His Gly Leu Cys Gly Glu Pro Gly
        35                  40                  45

Gln Cys Ile Cys Thr Asp Gly Trp Asp Gly Glu Leu Cys Asp Arg Asp
    50                  55                  60

Val Arg Ala Cys Ser Ser Ala Pro Cys Ala Asn Asn Gly Thr Cys Val
65                  70                  75                  80

Ser Leu Asp Asp Gly Leu Tyr Glu Cys Ser Cys Ala Pro Gly Tyr Ser
                85                  90                  95

Gly Lys Asp Cys Gln Lys Lys Asp Gly Pro Cys Val Ile Asn Gly Ser
            100                 105                 110

Pro Cys Gln His Gly Gly Thr Cys Val Asp Asp Glu Gly Arg Ala Ser
        115                 120                 125
```

```
His Ala Ser Cys Leu Cys Pro Pro Gly Phe Ser Gly Asn Phe Cys Glu
    130             135             140
Ile Val Ala Asn Ser Cys Thr Pro Asn Pro Cys Glu Asn Asp Gly Val
145             150             155             160
Cys Thr Asp Ile Gly Gly Asp Phe Arg Cys Arg Cys Pro Ala Gly Phe
                165             170             175
Ile Asp Lys Thr Cys Ser Arg Pro Val Thr Asn Cys Ala Ser Ser Pro
            180             185             190
Cys Gln Asn Gly Gly Thr Cys Leu Gln His Thr Gln Val Ser Tyr Glu
        195             200             205
Cys Leu Cys Lys Pro Glu Phe Thr Gly Leu Thr Cys Val Lys Lys Arg
    210             215             220
Ala Leu Ser Pro Gln Gln Val Thr Arg Leu Pro Ser Gly Tyr Gly Leu
225             230             235             240
Ala Tyr Arg Leu Thr Pro Gly Val His Glu Leu Pro Val Gln Gln Pro
                245             250             255
Glu His Arg Ile Leu Lys Val Ser Met Lys Glu Leu Asn Lys Lys Thr
            260             265             270
Pro Leu Leu Thr Glu Gly
        275
```